US006270800B1

(12) United States Patent
Speaker et al.

(10) Patent No.: US 6,270,800 B1
(45) Date of Patent: Aug. 7, 2001

(54) AQUEOUS SOLVENT BASED ENCAPSULATION OF A BOVINE HERPES VIRUS TYPE-1 SUBUNIT VACCINE

(75) Inventors: Tully J. Speaker; H. Fred Clark, both of Philadelphia; Charlotte A. Moser, Bensalem; Paul A. Offit, Bala Cynwyd, all of PA (US); Manuel Campos, Stonington, CT (US); Patrick J. Frenchick, Gurnee, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/063,676

(22) Filed: Apr. 21, 1998

Related U.S. Application Data

(60) Provisional application No. 60/044,172, filed on Apr. 23, 1997.

(51) Int. Cl.[7] .................... A61K 39/29

(52) U.S. Cl. .................... 424/489; 424/490; 424/491; 424/497; 424/199.1; 424/204.1; 424/229.1; 424/813

(58) Field of Search .................... 424/489, 490, 424/491, 497, 199.1, 204.1, 229.1, 813

(56) References Cited

U.S. PATENT DOCUMENTS 5,151,267 * 9/1992 Babiuk .
5,462,734 * 10/1995 Letchworth, III .
5,585,264 * 12/1996 Babiuk .
5,686,113 * 11/1997 Speaker .
5,858,989 * 1/1999 Babiuk .
5,879,895 * 3/1999 Babiuk .

FOREIGN PATENT DOCUMENTS

95/28227 * 10/1995 (WO) .

OTHER PUBLICATIONS

Van Drunen et al., 1994, Vaccine 12(14):1295–1302, "A subunit gIV vaccine, produced by transfected mammalian cells in culture, induces mucosal immunity against bovine herpesvirus–1 in cattle".

Tikoo et al., 1990, J. Virology 64(10):5132–5142, "Molecular cloning, sequencing, and expression of functional bovine herpesvirus 1 glycoprotein gIV in transfected bovine cells".

* cited by examiner

*Primary Examiner*—Marianne P. Allen
*Assistant Examiner*—Mary K Zeman
(74) *Attorney, Agent, or Firm*—Peter C. Richardson; Paul H. Ginsburg; Alan L. Koller

(57) ABSTRACT

A microencapsulated subunit component from bovine herpes virus-1 (BHV-1) is disclosed. Vaccines, kits, and methods for using the same to vaccinate a member of a bovine species are also disclosed.

19 Claims, 8 Drawing Sheets

FIG. 1A-1

```
GGGCCGCAGC CCCGGCTGGG TATATATCCC CGACGGGGCGA CTAGAGATAC ACTCGCCCCG   60

CGCGGCTGCT GCGAGCGGGC GAAC ATG CAA GGG CCG ACA TTG GCC GTG CTG       111
                           Met Gln Gly Pro Thr Leu Ala Val Leu
                            1                   5

GGC GCG CTC GCC GTT GCG GTG AGC TTG CCT ACA CCC GCG CCG CGG           159
Gly Ala Leu Ala Val Ala Val Ser Leu Pro Thr Pro Ala Pro Arg
 10                  15                  20                  25

GTG ACG GTA TAC GTC GAC CCG GAC CCG CCG GCG TAC CCG ATG CCG CGA TAC AAC  207
Val Thr Val Tyr Val Asp Pro Asp Pro Pro Ala Tyr Pro Met Pro Arg Tyr Asn
                 30                  35                           40

TAC ACT GAA CGC TGG CAC ACT ACC GGG CCC ATA CCG TCG CCC TTC GCA       255
Tyr Thr Glu Arg Trp His Thr Thr Gly Pro Ile Pro Ser Pro Phe Ala
             45                  50                  55

GAC GGC CGC GAG CAG CCC GTC GAG GTG CGC TAC GCG ACG AGC GCG GCG       303
Asp Gly Arg Glu Gln Pro Val Glu Val Arg Tyr Ala Thr Ser Ala Ala
         60                  65                  70

GCG TGC GAC ATG CTG GCG CTG ATC GCA GAC CCG CAG GTG GGG CGC ACG       351
Ala Cys Asp Met Leu Ala Leu Ile Ala Asp Pro Gln Val Gly Arg Thr
     75                  80                  85
```

FIG. 1A-2

```
CTG TGG GAA GCG GTA CGC CGG CAC GCG CGC TAC AAC GCC ACG GTC    399
Leu Trp Glu Ala Val Arg Arg His Ala Arg Tyr Asn Ala Thr Val
 90              95             100             105

ATA TGG TAC AAG ATC GAG AGC GGG TGC GCC CGG CCG CTG TAC ATG    447
Ile Trp Tyr Lys Ile Glu Ser Gly Cys Ala Arg Pro Leu Tyr Met
        110             115             120

GAG TAC ACC GAG TGC GAG CCC AGG AAG CAC TTT GGG TAC TGC TAC    495
Glu Tyr Thr Glu Cys Glu Pro Arg Lys His Phe Gly Tyr Cys Tyr
    125             130             135

CGC ACA CCC CCG TTT TGG GAC AGC ATT ATG GCC TTC CTG GCC TAC CCC    543
Arg Thr Pro Pro Phe Trp Asp Ser Ile Met Ala Phe Leu Ala Tyr Pro
140             145             150

ACG GAC GAG CTG GGA CTG GAG GAC AGC GCG GCG CCC GCG CTC GTC    591
Thr Asp Glu Leu Gly Leu Glu Asp Ser Ala Ala Pro Ala Leu Val
155             160             165

GAG GGC CAG TAC CGA CGC GCG CTG TAC ATC GAC GGC ACG GTC GCC TAT    639
Glu Gly Gln Tyr Arg Arg Ala Leu Tyr Ile Asp Gly Thr Val Ala Tyr
170             175             180             185
```

FIG. 1B-1

```
ACA GAT TTC ATG GTT TCG CTG CCG GCC GGG GAC TGC TGG TTC TCG AAA   687
Thr Asp Phe Met Val Ser Leu Pro Ala Gly Asp Cys Trp Phe Ser Lys
            190                 195                 200

CTC GGC GCG GCT CGC GGG TAC ACC TTT GGC GCG TGC TTC CCG GCC CCG   735
Leu Gly Ala Ala Arg Gly Tyr Thr Phe Gly Ala Cys Phe Pro Ala Arg
            205                 210                 215

GAT TAC GAG CAA AAG GTT CTG CGC CTG ACG TAT CTC ACG CAG TAC       783
Asp Tyr Glu Gln Lys Val Leu Arg Leu Thr Tyr Leu Thr Gln Tyr
        220                 225                 230

TAC CCG GAG GCA CAC AAG GCC ATA GTC GAC TAC TGG TTC ATG CGC       831
Tyr Pro Glu Ala His Lys Ala Ile Val Asp Tyr Trp Phe Met Arg
    235                 240                 245

CAC GGG GGC GTC GTT CCG TAT TTT GAG GAG TCG AAG GGC TAC GAG       879
His Gly Gly Val Val Pro Tyr Phe Glu Glu Ser Lys Gly Tyr Glu
        250                 255                 260                 265

CCG CCT GCC GCC GAT GGG GGT TCC CCC GCG CCA CCC GGC GAC GAC       927
Pro Pro Ala Ala Asp Gly Gly Ser Pro Ala Pro Pro Gly Asp Asp
        270                 275                 280
```

FIG. 1B-2

```
GAG GCC CGC GAG GAT GAA GGG GAG ACC GAG GAC GGG GCA GCC GGG CGG    975
Glu Ala Arg Glu Asp Glu Gly Glu Thr Glu Asp Gly Ala Ala Gly Arg
        285                 290                 295

GAG GGC AAC GGC GGC CCC CCA GGA CCC GAA GGC GAC GGC AGT CAG       1023
Glu Gly Asn Gly Gly Pro Pro Gly Pro Glu Gly Asp Gly Ser Gln
            300                 305                 310

ACC GAA GCC AAC GGA GCC GAG GGC GAG GGC GCC AAA CCC GGC CCC      1071
Thr Glu Ala Asn Gly Ala Glu Gly Glu Gly Ala Lys Pro Gly Pro
        315                 320                 325

AGC GAC GCC GAC CGC GAG GGC GAA TGG CCG AGC CTC GAA GCC ATC      1119
Ser Asp Ala Asp Arg Glu Gly Glu Trp Pro Ser Leu Glu Ala Ile
        330                 335                 340         345

ACG CAC CCC CCG CCC GCT ACG CCC GCT ACG CCC GCC GCC CCC GAC GCC GTG   1167
Thr His Pro Pro Pro Ala Thr Pro Ala Pro Ala Pro Asp Ala Val
        350                 355                 360

CCG GTC AGC GTC GGG ATC GGC ATT GCG GCT GCG GCG ATC GCG TGC GTG    1215
Pro Val Ser Val Gly Ile Gly Ile Ala Ala Ala Ala Ile Ala Cys Val
        365                 370                 375
```

FIG. 1C-1

```
GCC GCC GCC GCC GGC GCG TAC TTC GTC TAT ACG CGC CGG CGC GGT    1263
Ala Ala Ala Ala Gly Ala Tyr Phe Val Tyr Thr Arg Arg Arg Gly
        380                 385                 390

GCG GGT CTG CCC AGA AAG CCA AAA AAG CTG CCG GCC TTT GGC AAC    1311
Ala Gly Pro Leu Pro Arg Lys Pro Lys Lys Leu Pro Ala Phe Gly Asn
        395                 400                 405

GTC AAC TAC AGC ACG CTG CCC GGG TGAGCGGCCT AGGCCCTCCC CCGACCGCCC    1365
Val Asn Tyr Ser Ala Leu Pro Gly
        410                 415

CCTTTGCTCC TAGCCCCGGC TCCTGCCGAG CCGCGCGGGG    1405
```

FIG. 2

Anionic Polymers
- P-acrylic acid (74)
- p-vinylcarboxylic acid (86)
- alginic acid (176)
- Eudragit L-100 (185)
- cellulose sulfate (260)
- carboxymethylcellulose (295)
- heparin (480)
- chondroitin sulfate (480)
- cellulose acetate phthalate (563)
- arabic (1000)

Amines
- Ethylenediamine (30)
- triethylenetetramine (37)
- piperazine (43)
- spermine (51)
- arginine (87)
- triethylamine (95)
- decylamine (156)
- dodecylamine (170)
- tetradecylamine (184)
- methylene blue (187)
- hexadecylamine (198)
- octadecylamine (212)

| Amine | P-acrylic acid | p-vinylcarboxylic acid | alginic acid | Eudragit L-100 | cellulose sulfate | carboxymethyl- cellulose | heparin | chondroitin sulfate | cellulose acetate phthalate | arabic |
|---|---|---|---|---|---|---|---|---|---|---|
| Ethylenediamine | o | o | o | o | o | o | + | + | o | + |
| triethylenetetramine | + | + | o | + | + | + | + | + | + | + |
| piperazine | o | o | o | + | o | o | + | + | o | + |
| spermine | o | + | o | + | o | o | + | + | o | + |
| arginine | o | o | o | + | o | o | + | + | o | + |
| triethylamine | + | + | o | + | o | o | + | + | + | + |
| decylamine | o | o | o | + | o | o | + | + | o | + |
| dodecylamine | o | + | + | + | o | o | + | + | + | + |
| tetradecylamine | + | + | o | + | + | + | + | + | + | + |
| hexadecylamine | + | + | o | + | o | o | + | + | o | + |

FIG. 3

| Amines | P-acrylic acid (74) | p-vinylcarboxylic acid (86) | alginic acid (176) | Eudragit L-100 (185) | cellulose sulfate (260) | carboxymethylcellulose (295) | heparin (480) | chondroitin sulfate (480) | cellulose acetate phthalate (563) | arabic (1000) |
|---|---|---|---|---|---|---|---|---|---|---|
| Ethylenediamine (30) | o | o | o | o | o | o | + | + | + | o |
| triethylenetetramine (37) | o | o | o | o | o | o | o | o | o | o |
| piperazine (43) | o | o | o | + | o | o | + | + | + | o |
| spermine (51) | o | o | o | + | o | o | + | + | + | o |
| arginine (87) | o | o | o | + | o | o | + | + | + | o |
| triethylamine (95) | + | + | o | + | o | o | + | + | + | + |
| decylamine (156) | o | o | o | + | o | o | + | + | + | o |
| dodecylamine (170) | o | + | + | + | o | o | + | + | + | + |
| tetradecylamine (184) | + | + | o | + | + | o | + | + | + | + |
| methylene blue (187) | + | + | o | + | + | o | + | + | + | + |
| hexadecylamine (198) | + | + | o | + | o | + | + | + | + | o |
| octadecylamine (212) | + | + | o | + | o | + | + | + | + | o |

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1405 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 85..1335

(xi) SEQUENCE DESCRIPTION: SEQ ID NO:1:

```
GGGCCGCAGC CCCGGCTGGG TATATATCCC CGACGGGCGA CTAGAGATAC ACTCGCCCCG      60

CGCGGCTGCT GCGAGCGGGC GAAC ATG CAA GGG CCG ACA TTG GCC GTG CTG       111
                            Met Gln Gly Pro Thr Leu Ala Val Leu
                              1               5

GGC GCG CTG CTC GCC GTT GCG GTG AGC TTG CCT ACA CCC GCG CCG CGG      159
Gly Ala Leu Leu Ala Val Ala Val Ser Leu Pro Thr Pro Ala Pro Arg
         10              15                  20                  25
```

```
GTG ACG GTA TAC GTC GAC CCG CCG GCG TAC CCG ATG CCG CGA TAC AAC         207
Val Thr Val Tyr Val Asp Pro Pro Ala Tyr Pro Met Pro Arg Tyr Asn
            30                      35                      40

TAC ACT GAA CGC TGG CAC ACT ACC GGG CCC ATA CCG TCG CCC TTC GCA         255
Tyr Thr Glu Arg Trp His Thr Thr Gly Pro Ile Pro Ser Pro Phe Ala
        45                      50                      55

GAC GGC CGC GAG CAG CCC GTC GAG GTG CGC TAC GCG ACG AGC GCG GCG         303
Asp Gly Arg Glu Gln Pro Val Glu Val Arg Tyr Ala Thr Ser Ala Ala
            60                      65                      70

GCG TGC GAC ATG CTG GCG CTG ATC GCA GAC CCG CAG GTG GGG CGC ACG         351
Ala Cys Asp Met Leu Ala Leu Ile Ala Asp Pro Gln Val Gly Arg Thr
        75                      80                      85

CTG TGG GAA GCG GTA CGC CGG CAC GCG CGC GCG TAC AAC GCC ACG GTC         399
Leu Trp Glu Ala Val Arg Arg His Ala Arg Ala Tyr Asn Ala Thr Val
 90                      95                     100                     105

ATA TGG TAC AAG ATC GAG AGC GGG TGC GCC CGG CCG CTG TAC TAC ATG         447
Ile Trp Tyr Lys Ile Glu Ser Gly Cys Ala Arg Pro Leu Tyr Tyr Met
                    110                     115                     120

GAG TAC ACC GAG TGC GAG CCC AGG AAG CAC TTT GGG TAC TGC CGC TAC         495
Glu Tyr Thr Glu Cys Glu Pro Arg Lys His Phe Gly Tyr Cys Arg Tyr
            125                     130                     135

CGC ACA CCC CCG TTT TGG GAC AGC TTC CTG GCG GGC TTC GCC TAC CCC         543
Arg Thr Pro Pro Phe Trp Asp Ser Phe Leu Ala Gly Phe Ala Tyr Pro
            140                     145                     150

ACG GAC GAC GAG CTG GGA CTG ATT ATG GCG GCG CCC GCG CGG CTC GTC         591
Thr Asp Asp Glu Leu Gly Leu Ile Met Ala Ala Pro Ala Arg Leu Val
        155                     160                     165

GAG GGC CAG TAC CGA CGC GCG CTG TAC ATC GAC GGC ACG GTC GCC TAT         639
Glu Gly Gln Tyr Arg Arg Ala Leu Tyr Ile Asp Gly Thr Val Ala Tyr
170                     175                     180                     185

ACA GAT TTC ATG GTT TCG CTG CCG GCC GGG GAC TGC TGG TTC TCG AAA         687
Thr Asp Phe Met Val Ser Leu Pro Ala Gly Asp Cys Trp Phe Ser Lys
                    190                     195                     200

CTC GGC GCG GCT CGC GGG TAC ACC TTT GGC GCG TGC TTC CCG GCC CGG         735
Leu Gly Ala Ala Arg Gly Tyr Thr Phe Gly Ala Cys Phe Pro Ala Arg
            205                     210                     215

GAT TAC GAG CAA AAG AAG GTT CTG CGC CTG ACG TAT CTC ACG CAG TAC         783
Asp Tyr Glu Gln Lys Lys Val Leu Arg Leu Thr Tyr Leu Thr Gln Tyr
        220                     225                     230

TAC CCG CAG GAG GCA CAC AAG GCC ATA GTC GAC TAC TGG TTC ATG CGC         831
Tyr Pro Gln Glu Ala His Lys Ala Ile Val Asp Tyr Trp Phe Met Arg
        235                     240                     245

CAC GGG GGC GTC GTT CCG CCG TAT TTT GAG GAG TCG AAG GGC TAC GAG         879
His Gly Gly Val Val Pro Pro Tyr Phe Glu Glu Ser Lys Gly Tyr Glu
250                     255                     260                     265

CCG CCG CCT GCC GCC GAT GGG GGT TCC CCC GCG CCA CCC GGC GAC GAC         927
Pro Pro Pro Ala Ala Asp Gly Gly Ser Pro Ala Pro Pro Gly Asp Asp
            270                     275                     280

GAG GCC CGC GAG GAT GAA GGG GAG ACC GAG GAC GGG GCA GCC GGG CGG         975
Glu Ala Arg Glu Asp Glu Gly Glu Thr Glu Asp Gly Ala Ala Gly Arg
            285                     290                     295

GAG GGC AAC GGC GGC CCC CCA GGA CCC GAA GGC GAC GGC GAG AGT CAG        1023
Glu Gly Asn Gly Gly Pro Pro Gly Pro Glu Gly Asp Gly Glu Ser Gln
            300                     305                     310

ACC CCC GAA GCC AAC GGA GGC GCC GAG GGC GAG CCG AAA CCC GGC CCC        1071
Thr Pro Glu Ala Asn Gly Gly Ala Glu Gly Glu Pro Lys Pro Gly Pro
        315                     320                     325

AGC CCC GAC GCC GAC CGC CCC GAA GGC TGG CCG AGC CTC GAA GCC ATC        1119
Ser Pro Asp Ala Asp Arg Pro Glu Gly Trp Pro Ser Leu Glu Ala Ile
```

```
330              335              340              345
ACG CAC CCC CCG CCC GCC CCC GCT ACG CCC GCG GCC CCC GAC GCC GTG    1167
Thr His Pro Pro Pro Ala Pro Ala Thr Pro Ala Ala Pro Asp Ala Val
            350              355              360

CCG GTC AGC GTC GGG ATC GGC ATT GCG GCT GCG GCG ATC GCG TGC GTG    1215
Pro Val Ser Val Gly Ile Gly Ile Ala Ala Ala Ala Ile Ala Cys Val
            365              370              375

GCC GCC GCC GCC GCC GGC GCG TAC TTC GTC TAT ACG CGC CGG CGC GGT    1263
Ala Ala Ala Ala Ala Gly Ala Tyr Phe Val Tyr Thr Arg Arg Arg Gly
            380              385              390

GCG GGT CCG CTG CCC AGA AAG CCA AAA AAG CTG CCG GCC TTT GGC AAC    1311
Ala Gly Pro Leu Pro Arg Lys Pro Lys Lys Leu Pro Ala Phe Gly Asn
395              400              405

GTC AAC TAC AGC GCG CTG CCC GGG TGAGCGGCCT AGGCCCTCCC CCGACCGCCC   1365
Val Asn Tyr Ser Ala Leu Pro Gly
410             415

CCTTTGCTCC TAGCCCCGGC TCCTGCCGAG CCGCGCGGGG                        1405

(2) INFORMATION FOR SEQ ID NO:2:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Gly Pro Thr Leu Ala Val Leu Gly Ala Leu Leu Ala Val Ala
1               5                   10                  15

Val Ser Leu Pro Thr Pro Ala Pro Arg Val Thr Val Tyr Val Asp Pro
                20                  25                  30

Pro Ala Tyr Pro Met Pro Arg Tyr Asn Tyr Thr Glu Arg Trp His Thr
            35                  40                  45

Thr Gly Pro Ile Pro Ser Pro Phe Ala Asp Gly Arg Glu Gln Pro Val
        50                  55                  60

Glu Val Arg Tyr Ala Thr Ser Ala Ala Cys Asp Met Leu Ala Leu
65                  70                  75                  80

Ile Ala Asp Pro Gln Val Gly Arg Thr Leu Trp Glu Ala Val Arg Arg
                85                  90                  95

His Ala Arg Ala Tyr Asn Ala Thr Val Ile Trp Tyr Lys Ile Glu Ser
                100                 105                 110

Gly Cys Ala Arg Pro Leu Tyr Tyr Met Glu Tyr Thr Glu Cys Glu Pro
            115                 120                 125

Arg Lys His Phe Gly Tyr Cys Arg Tyr Arg Thr Pro Pro Phe Trp Asp
        130                 135                 140

Ser Phe Leu Ala Gly Phe Ala Tyr Pro Thr Asp Asp Glu Leu Gly Leu
145                 150                 155                 160

Ile Met Ala Ala Pro Ala Arg Leu Val Glu Gly Gln Tyr Arg Arg Ala
                165                 170                 175

Leu Tyr Ile Asp Gly Thr Val Ala Tyr Thr Asp Phe Met Val Ser Leu
            180                 185                 190

Pro Ala Gly Asp Cys Trp Phe Ser Lys Leu Gly Ala Ala Arg Gly Tyr
            195                 200                 205

Thr Phe Gly Ala Cys Phe Pro Ala Arg Asp Tyr Glu Gln Lys Lys Val
        210                 215                 220

Leu Arg Leu Thr Tyr Leu Thr Gln Tyr Tyr Pro Gln Glu Ala His Lys
```

-continued

```
               225                 230                 235                 240
Ala Ile Val Asp Tyr Trp Phe Met Arg His Gly Gly Val Val Pro Pro
                    245                 250                 255
Tyr Phe Glu Glu Ser Lys Gly Tyr Glu Pro Pro Ala Ala Asp Gly
                260                 265                 270
Gly Ser Pro Ala Pro Pro Gly Asp Asp Glu Ala Arg Glu Asp Glu Gly
            275                 280                 285
Glu Thr Glu Asp Gly Ala Ala Gly Arg Glu Gly Asn Gly Gly Pro Pro
        290                 295                 300
Gly Pro Glu Gly Asp Gly Glu Ser Gln Thr Pro Glu Ala Asn Gly Gly
305                 310                 315                 320
Ala Glu Gly Glu Pro Lys Pro Gly Pro Ser Pro Asp Ala Asp Arg Pro
                325                 330                 335
Glu Gly Trp Pro Ser Leu Glu Ala Ile Thr His Pro Pro Pro Ala Pro
                340                 345                 350
Ala Thr Pro Ala Ala Pro Asp Ala Val Pro Val Ser Val Gly Ile Gly
            355                 360                 365
Ile Ala Ala Ala Ala Ile Ala Cys Val Ala Ala Ala Ala Gly Ala
        370                 375                 380
Tyr Phe Val Tyr Thr Arg Arg Arg Gly Ala Gly Pro Leu Pro Arg Lys
385                 390                 395                 400
Pro Lys Lys Leu Pro Ala Phe Gly Asn Val Asn Tyr Ser Ala Leu Pro
                405                 410                 415
Gly
```

AQUEOUS SOLVENT BASED ENCAPSULATION OF A BOVINE HERPES VIRUS TYPE-1 SUBUNIT VACCINE

This application claims the benefit under 35 USC § 119(e) of U.S. provisional application Ser. No. 60/044,172, which was filed on Apr. 23, 1997.

FIELD OF THE INVENTION

The present invention relates to microencapsulated vaccines. More particularly, the present invention relates to novel microcapsules having an anisotropic salt membrane encapsulating an aqueous or substantially aqueous core together with an immunogenic composition. The microcapsules are prepared by the interfacial reaction, in aqueous medium, of Lewis acid and base wall-forming reactants. More particularly, the present invention relates to a subunit component of bovine herpes virus-1 (BHV-1) so encapsulated.

BACKGROUND OF THE INVENTION

Microencapsulation is a process by which a relatively thin coating can be applied to dispersions of small particles of solids or droplets of liquids, thus providing a means for converting liquids to solids, altering colloidal and surface properties, providing environmental protection, and controlling the release characteristics or availability of coated materials. Several of these properties can be attained by macropackaging techniques; however, the uniqueness of microencapsulation is the smallness of the coated particles and their subsequent use and adaptation to a wide variety of dosage forms and product applications. Heretofore, known feasible methods for producing microcapsules on an industrial scale have often involved the use of organic solvents. However, the use of organic solvents may present environmental and safety problems. In addition, it is often difficult to remove all the organic solvent from the microcapsules, thus leaving organic contaminants.

It has been proposed to use microcapsules as a means of delivering vaccine. Two broad types of antigen delivery systems have been studied for their capacity to enhance immunity: solid (or porous) microcapsules and microcapsules with a core region surrounded by a physically distinct wall. Solid microcapsules may be prepared by a variety of processes including coacervation of colloids (Kwok, K.K., et al., 1991, *Pharm. Res.* 8:341–344), precipitation of proteins by physical means (e.g., phase separation) (Santiago, N., et al., 1993, *Pharm. Res.* 10:1243–1247) or chemical agents (e.g., acid chlorides) (Levy, M. C., et al., 1991, *J. Pharm. Sci.* 80:578–585.), or solvent evaporation techniques that surround aqueous dispersions with polyester films (Singh, M., et al., 1991, *Pharm. Res.* 8:958–961). Wall/core systems shown useful for antigen delivery include liposomes (Gerlier, D., et al., 1983, *J. Immunol.* 131:490), ISCOMS (Claassen, I., and Osterhaus, A., 1992, *Res. Immunol.* 143:531–541) and proteosomes (Gould-Fogerite, S., and Mannino, R., 1992, *Liposome Technology,* Vol. III, Gregoriadis, G. (ed.), CRC Press, Boca Raton, Fla.; Miller, M. D., et al., 1992, *J. Exp. Med.* 176:1739–1744).

Perhaps the best studied of the antigen delivery systems are those derived from the linear polymeric esters of lactic acid and glycolic acid (i.e., poly (DL-lactide-co-glycolide)) (PLCG) (Edelman, R., et al., 1993, *Vaccine* 11:155–158; Eldridge, J. H., et al., 1989, *Curr. Top. Microbiol. Immunol.* 146:59–66; Eldridge, J. H. et al., 1990, *J. Controlled Release* 11:205–214; Eldridge, J. H., et al., 1989, *Adv. Exp. Med. Biol.* 251:191–202; Eldridge, J. H., et al., 1991, *Mol. Immunol.* 28:287–294; Eldridge, J. H., et al., 1991, *Infect. Immun.* 59:2978–2986; Marx, P. A., et al., 1993, *Science* 260:1323–1327; Moldoveanu, Z., et al., 1993, *J. Infect. Dis.* 167:84–90; O'Hagan, D. T., et al., 1993, *Vaccine* 11:149–154; O'Hagan, D. T., et al., 1991, *Immunology* 73: 239–242; Ray, R., et al., 1993, *J. Infect. Dis.* 167:752–755; Reid, R., et al., 1993, *J. Immunol.* 150:323A; Reid, R. H., et al., 1993, *Vaccine* 11:159–167). Encapsulation of putative antigens into PLCG microcapsules affords a number of advantages. First, microcapsules are easily degraded by hydrolysis to form lactic acid and glycolic acid. Second, PLCG microcapsules less than 5 $\mu$m in size readily penetrate Peyer's patches, mesenteric lymph nodes and spleen after oral inoculation of mice. Third, oral, intraperitoneal, intranasal or subcutaneous inoculation of mice with PLCG microencapsulated antigens including influenza virus, parainfluenza virus, simian immunodeficiency virus, *Staph. aureus* enterotoxin B toxoid, and ovalbumin induces a greater immune response than that induced in animals inoculated with the same dose of free virus or protein. In addition, oral inoculation of mice with inactivated viruses induces an enhanced antigen-specific IgA response at mucosal surfaces. Lastly, PLCG microcapsules have been administered orally to adult volunteers without adverse effects.

The major disadvantage of PLCG microcapsules is the requisite use of organic solvents. Contact with organic solvents will inactivate the infectivity of viral and bacterial pathogens, and, in addition, may alter the immunogenicity of surface proteins critical to induction of humoral or cellular immune responses. In fact, large quantities of viral proteins have been required to induce an antigen-specific immune response with PLCG microcapsules.

Microencapsulation techniques are generally disclosed in U.S. Pat. No. 3,137,631; U.S. Pat. No. 4,205,060; U.S. Pat. No. 4,606,940; U.S. Pat. No. 3,959,457; and U.S. Pat. No. 5,132,117. In addition, microencapsulation techniques are taught in Belgium Pat. 882,476 to Lim (1980); U.S. Pat. No. 4,744,933; and U.K. Pat. Appl. 2 135 954 A to Dautzenberg et al. (1984). However, these techniques have drawbacks, including the use of organic solvents or heat, which can lead to inactivation or denaturation of the antigen. More specifically, most methods for preparing immunogens such as vaccines in encapsulated form (e.g., PLGA's, cochleates, liposomes) require multiple, often harsh, processing steps (e.g., introduction of surface active agents, generation of liquid/liquid interfaces with different surface energies, dispersion in reactive organic liquid phases, mechanical shearing during emulsification and/or vortexing, heating to remove one or another volatile components). Each of the several processing steps can exert an adverse influence on functional integrity of some or all of the initial quantity of immunogen used in the encapsulation. Such a reduction in functional integrity of some fraction of the initial charge of immunogen is manifested in reduced stability and immunogenicity of the resulting formulation, and counters the desired enhancement of immune response sought through encapsulation. With agents of low immunogenicity, the toll taken by multiple harsh processing steps may defeat any benefits to be derived by encapsulation using methods already known in the art.

By contrast, International Publication WO 95/28227 describes a microencapsulation technology that utilizes an all-aqueous system. This technology is based on the formation of poorly soluble (amine) salts of polyanionic macromolecules. Using this technology, immunogenic compositions are encapsulated using an entirely aqueous system of reagents at or below room temperature and without need for high pressures. This process is capable of producing uniform size particles under very gentle conditions, and may be used to microencapsulate immunogenic compositions from infectious agents for use in vaccines.

An infectious agent of particular interest for encapsulation using the above-described all-aqueous system is bovine herpesvirus-1 (BHV-1), also known as infectious bovine rhinotracheitis virus. BHV-1 is a member of the alphaherpesviridae subfamily, and produces a variety of clinical forms of disease in cattle, including respiratory and genital infections, conjunctivitis, encephalitis, and abortions. Previous attempts at controlling BHV-1 infection have utilized vaccines comprising live attenuated virus (Gerber, J. D., et al., 1978, Am. J. Vet. Res. 39:753–760; Mitchell, D., 1974, Can. Vet. Jour. 15:148–151), inactivated virus (Frerichs, G. N., et al., 1982, Vet. Rec. 111:116–122), and viral subunits such as, e.g., one of the three major BHV-1 glycoproteins, which have been designated in the art as gI, gIII, and gIV (Babiuk, L. A., et al., 1987, Virology 159:57–66; van Drunen, S., et al., 1993, Vaccine 11:25–35). In addition, the ability of a recombinant, truncated version of the BHV-1 gIV glycoprotein (designated in the art as BHV-1 tgIV) to induce mucosal immunity against BHV-1 has been demonstrated (van Drunen, S., et al., 1994, Vaccine, 12:1295–1302). However, the immunoresponse to BHV-1 tgIV is low, requiring the administration of either large amounts of immunogen, which may be commercially impractical, or the addition of a potent adjuvant, which may in turn induce undesirable injection-site reactions. It was not known whether immunogenicity of a BHV-1 subunit component generally, and BHV-1 tgIV in particular, could be significantly enhanced by microencapsulation.

SUMMARY OF THE INVENTION

The present invention provides stable microcapsules that have aqueous cores and include immunogenic compositions comprising a subunit component of BHV-1. The microcapsules of the invention are produced according to methods based on those described in International Publication WO 95/28227, which is incorporated herein by reference in its entirety. These microcapsules are substantially free of non-aqueous contaminants. The invention further provides a highly efficient method of preparing such microcapsules.

In a first aspect, the present invention provides a microcapsule comprising an anisotropic Lewis salt membrane encapsulating an aqueous or substantially aqueous core and an immunogenic composition surrounded by the salt membrane, said microcapsule being substantially free of non-aqueous contaminants, said salt membrane comprising a precipitate resulting from the interfacial reaction of a selected water-soluble anionic polymer with a selected water-soluble amine, or the interfacial reaction of a water-soluble neutral salt of a selected anionic polymer with a water-soluble neutral salt of a selected amine. In a preferred embodiment, the selected anionic polymer is alginic acid, which is preferably in the form of a corresponding water-soluble, neutral salt (e.g., sodium alginate), and the selected amine is spermine, which is preferably in the form of a corresponding water-soluble, neutral salt (e.g., spermine hydrochloride).

The immunogenic composition comprises a subunit component of BHV-1 which is capable of inducing a protective immune response against BHV-1 when administered in the encapsulated form of the invention to a member of a bovine species. In a preferred embodiment, the subunit component of the immunogenic composition of the microcapsule comprises a BHV-1 glycoprotein such as, e.g., gI, gIII or gIV, or an immunogenic fragment or derivative thereof. In a more preferred embodiment, the immunogenic composition of the microcapsule comprises a truncated BHV-1 glycoprotein, such as, e.g., BHV-1 tgIV (designated hereinafter as BHV-1-gD). In a more preferred embodiment, the immunogenic composition of the microcapsule is BHV-1-gD.

In a second aspect, the present invention provides a method of increasing the immunogenicity of a subunit component of BHV-1, comprising encapsulating said BHV-1 subunit component in a microcapsule comprising an anisotropic Lewis salt membrane encapsulating an aqueous or substantially aqueous core, said microcapsule being substantially free of non-aqueous contaminants, said salt membrane comprising a precipitate resulting from the interfacial reaction of a selected water-soluble anionic polymer with a selected water-soluble amine, or the interfacial reaction of a water-soluble neutral salt of a selected anionic polymer with a water-soluble neutral salt of a selected amine. In a preferred embodiment, the selected anionic polymer is alginic acid, which is preferably in the form of a corresponding water-soluble, neutral salt (e.g., sodium alginate), and the selected amine is spermine, which is preferably in the form of a corresponding water-soluble, neutral salt (e.g., spermine hydrochloride).

In a preferred embodiment, the BHV-1 subunit component comprises a BHV-1 glycoprotein such as, e.g., gI, gIII or gIV, or an immunogenic fragment or derivative thereof. In a more preferred embodiment, the BHV-1 subunit component comprises a truncated BHV-1 glycoprotein, such as, e.g., BHV-1-gD. In a more preferred embodiment, the BHV-1 subunit component of the method is BHV-1-gD.

In a third aspect, the present invention provides a vaccine for protecting a member of a bovine species against BHV-1, comprising an immunogenic amount of the microcapsules of the invention. The vaccine may further comprise a pharmaceutically or veterinarily acceptable carrier or diluent, and, optionally, an adjuvant.

In a fourth aspect, the present invention provides a method of vaccinating a member of a bovine species against BHV-1, comprising administering to the animal a vaccine comprising an immunogenic amount of the microcapsules of the invention.

In a fifth aspect, the present invention provides a kit for vaccinating a member of a bovine species against BHV-1, comprising a first container comprising an immunogenic amount of the microcapsules of the invention; and a second container comprising a pharmaceutically or veterinarily acceptable carrier or diluent. The microcapsules of the kit may optionally be supplied in lyophilized form. The kit may also optionally comprise an adjuvant.

In a sixth aspect, the present invention provides a combination vaccine for protecting a member of a bovine species against BHV-1 and, optionally, another disease or pathological condition, which combination vaccine comprises an immunogenic amount of the microcapsules of the invention; and an immunogenic amount of a second immunogenic composition capable of inducing a protective response against a disease or pathological condition in the member of the bovine species. The combination vaccine may further comprise a pharmaceutically or veterinarily acceptable carrier or diluent, and, optionally, an adjuvant.

BRIEF DESCRIPTION OF THE FIGURES

FIGS. 1 (1A–1 through 1C–1) is the nucleotide sequence encoding BHV-1 glycoprotein IV (SEQ ID NO: 1), and its deduced amino acid sequence (SEQ ID NO: 2). BHV-1-gD (i.e., tgIV) extends from amino acid residue 19 to residue 355.

FIG. 2 demonstrates amine/polymer combinations which form insoluble salts according to the invention. A plus (+) mark indicates formation of a precipitate when reactants are combined. A zero (0) indicates that no precipitate forms.

FIG. 3 demonstrates amine/polymer combinations which form stable microcapsules according to the invention. A plus (+) mark indicates that the reactants do form microcapsules. A zero (0) indicates that they do not.

FIG. 4 is a schematic side view of an apparatus used in the preferred method for making the microcapsular material of the present invention.

DETAILED DESCRIPTION OF THE INVENTION

Figure 4:
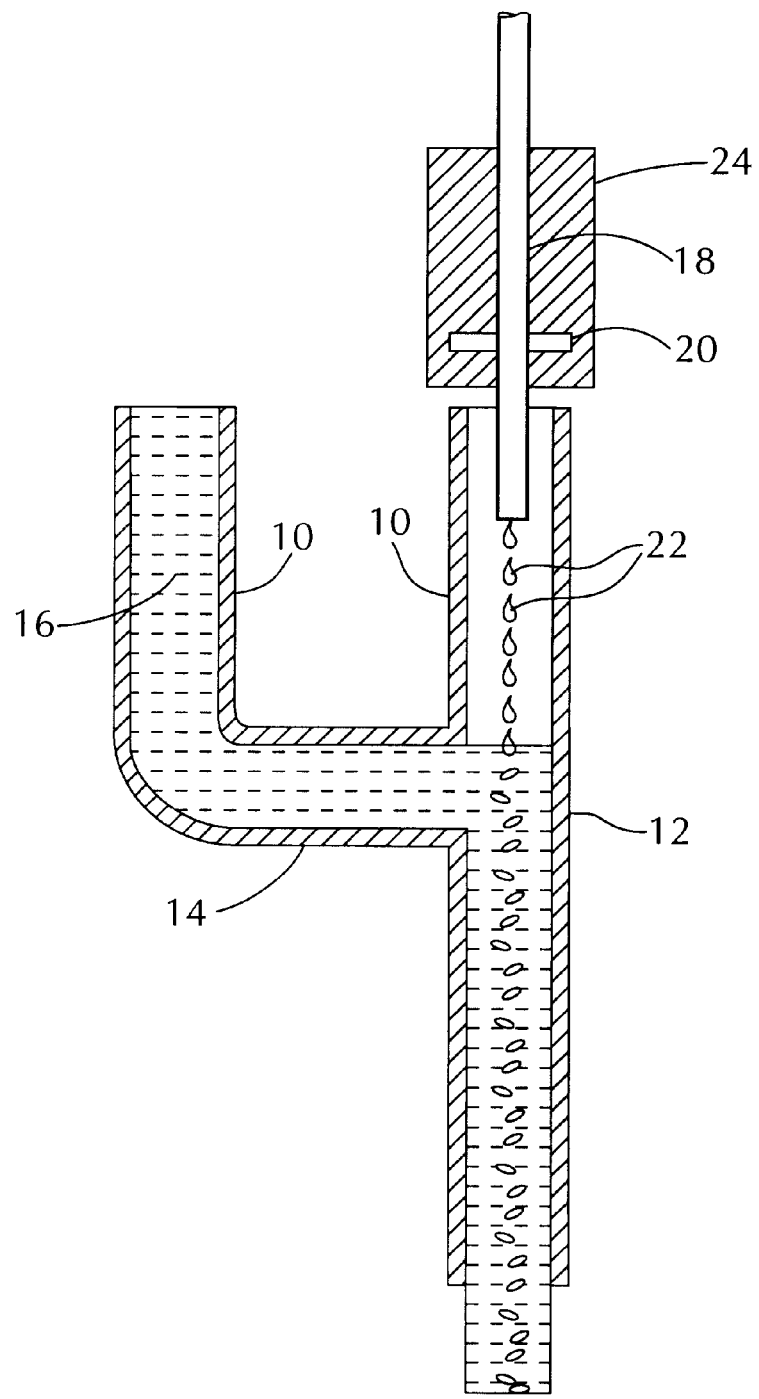

Applicants have surprisingly discovered that the immunogenicity of a BHV-1 subunit component is dramatically increased by microencapsulation. Specifically, Applicants have discovered that microencapsulation in spermine-alginate of a truncated form of the gIV glycoprotein of BHV-1 results in significantly increased immunogenicity compared to an unencapsulated control. Although microencapsulation has previously been shown to enhance the immunogenicity of other immunogens, no previous report reasonably predicted the observed degree of increase in immunogenicity of this BHV-1 subunit component resulting from encapsulation, as exemplified below.

Accordingly, the present invention provides a microcapsule, comprising an anisotropic Lewis salt membrane encapsulating an aqueous or substantially aqueous core and an immunogenic composition surrounded by the salt membrane, said microcapsule being substantially free of non-aqueous contaminants, said salt membrane comprising a precipitate resulting from the interfacial reaction of a selected water-soluble anionic polymer with a selected water-soluble amine, or the interfacial reaction of a water-soluble neutral salt of a selected anionic polymer with a water-soluble neutral salt of a selected amine, and said immunogenic composition comprising a subunit component of BHV-1 capable of inducing a protective response against BHV-1 when administered in the encapsulated form of the invention to a member of a bovine species.

The invention encompasses the use of a combination of any water-soluble anionic polymer with any water-soluble amine, or a combination of any water-soluble, neutral salt of an anionic polymer with any water-soluble, neutral salt of an amine, where the combination reacts to form stable microcapsules that can encapsulate and enhance the immunogenicity of the immunogenic composition of the invention.

In a preferred embodiment, the selected water-soluble anionic polymer is alginic acid and the selected water-soluble amine is spermine. Encapsulation of the immunogenic composition of the invention may be carried out by using alginic acid and spermine directly or, preferably, by using a corresponding water-soluble neutral salt of alginic acid and a corresponding water-soluble neutral salt of spermine. Such neutral salts of alginic acid and spermine are intended to include any neutral salts known in the art. In a preferred embodiment, encapsulation of the immunogenic composition of the invention is carried out by reacting the neutral sodium salt of alginic acid with the neutral hydrochloride salt of spermine.

In a further preferred embodiment, the subunit component of the immunogenic composition of the microcapsule comprises a BHV-1 glycoprotein such as, e.g., gI, gIII or gIV, or an immunogenic fragment or derivative thereof. In a more preferred embodiment, the immunogenic composition of the microcapsule comprises a truncated BHV-1 glycoprotein, such as, e.g., BHV-1-gD. In a more preferred embodiment, the immunogenic component of the microcapsule is BHV-1-gD.

The present invention further provides a method of increasing the immunogenicity of a subunit component of BHV-1, comprising encapsulating said BHV-1 subunit component in a microcapsule comprising an anisotropic Lewis salt membrane encapsulating an aqueous or substantially aqueous core, said microcapsule being substantially free of non-aqueous contaminants, said salt membrane comprising a precipitate resulting from the interfacial reaction of a selected water-soluble anionic polymer with a selected water-soluble amine, or the interfacial reaction of a water-soluble neutral salt of a selected anionic polymer with a water-soluble neutral salt of a selected amine. In a preferred embodiment, the selected anionic polymer is alginic acid, which is preferably in the form of a corresponding water-soluble, neutral salt (e.g., sodium alginate), and the selected amine is spermine, which is preferably in the form of a corresponding water-soluble, neutral salt (e.g., spermine hydrochloride).

In a further preferred embodiment, the BHV-1 subunit component of the method comprises a BHV-1 glycoprotein such as, e.g., gI, gIII or gIV, or an immunogenic fragment or derivative thereof. In a more preferred embodiment, the BHV-1 subunit component comprises a truncated BHV-1 glycoprotein, such as, e.g., BHV-1-gD. In a more preferred embodiment, the BHV-1 subunit component of the method is BHV-1-gD.

The Immunogenic Composition:

As used herein, a "BHV-1 subunit component" refers to any structural component (peptide, protein, glycoprotein, polysaccharide, lipoprotein, etc.) comprising the capsid or envelope of BHV-1, or any fragment or derivative thereof, or any nucleic acid polymer (DNA or RNA) encoding said structural component or fragment thereof, which is capable of directly or indirectly inducing a protective response against BHV-1 in a member of a bovine species when administered in encapsulated form according to the present invention. The BHV-1 subunit component may or may not be capable of inducing a protective immune response against BHV-1 when administered in an unencapsulated form to a member of a bovine species. The subunit component may be used in non-glycosylated form, or may be partially or fully glycosylated, or may have a different glycosylation pattern, compared to its native form.

BHV-1 may be isolated from tissues or organs of infected animals according to known techniques and propagated in susceptible cell cultures. See, e.g., van Drunen, 1994, supra. Alternatively, BHV-1 may be obtained from the American Type Culture Collection (ATCC). For example, the ATCC lists several BHV-1 strains, including strains having ATCC accession Nos. VR-631, VR-793, VR-2112, and VR-864, among others.

A variety of different subunit components of BHV-1, including their amino acid sequences and nucleotide sequences encoding them, are known in the art. For example, U.S. Pat. No. 5,151,267 to Babiuk et al. discloses the nucleotide sequences and deduced amino acid sequences of BHV-1 gI, gIII, and gIV. See also U.S. Pat. No. 5,585,264 to Babiuk et al. In addition, U.S. Pat. No. 5,545,523 to Batt et al. discloses BHV-1 -specific oligonucleotides useful in the amplification of BHV-1 gI and gIV gene sequences.

Furthermore, methods of purifying BHV-1 glycoproteins from virus-infected cell cultures have been described (Babiuk, L. A., et al., 1987, supra). These patents and publications are incorporated herein by reference.

van Drunen, et al., 1994, supra, describes the production of BHV-1 tgIV (i.e., BHV-1-gD), which is a truncated version of the gIV glycoprotein. BHV-1-gD was produced in transfected Madin Darby bovine kidney (MDBK) cells. MDBK cells are available from the ATCC (ATCC accession No. CCL22). The nucleotide sequence encoding the intact BHV-1 gIV glycoprotein (SEQ ID NO: 1) and its deduced amino acid sequence (SEQ ID NO: 2) are disclosed in U.S. Pat. No. 5,151,267 to Babiuk et al., and in Tikoo, S. K., et al., 1990, J. Virol. 64:5132–5142, and are presented herein in FIG. 1. BHV-1-gD is a portion of BHV-1 gIV, and consists of 337 amino acids, beginning at amino acid residue No. 19 (Leu) of gIV, and terminating with amino acid residue No. 355 (Pro).

Production of BHV-1-gD or other BHV-1 subunit components for use in the claimed invention may be carried out according to recombinant techniques described in the above-cited references, or as described more generally in the art. See, for example, Maniatis, et al., 1989, *Molecular cloning, a laboratory manual,* Cold Spring Harbor Laboratory Press, Cold Spring Harbor, N.Y.; Ausubel, et al., 1989, *Current protocols in molecular biology,* Greene Publishing Associates & Wiley Interscience, N.Y.; Sambrook, et al., 1989, *Molecular cloning: a laboratory manual,* 2d ed., Cold Spring Harbor Laboratory Press, Cold Spring Harbor, N.Y.; and Innis et al. (eds) 1995, *PCR strategies,* Academic Press, Inc., San Diego. All of the above-cited references are incorporated herein by reference in their entirety.

The use of fragments and derivatives of BHV-1 subunit components are also within the scope of the invention where such fragments and derivatives are capable of inducing a protective response against BHV-1 when administered in encapsulated form according to the present invention. Such immunogenic fragments and derivatives can be produced by various methods known in the art. The manipulations which result in their production can occur either at the gene level or the protein level, or both. At the gene level, e.g., a cloned DNA molecule encoding a BHV-1 subunit component can be modified in vitro by any of several known strategies. See, e.g., Maniatis, et al., 1989, supra; Ausubel, et al., 1989, supra; and Sambrook, et al., 1989, supra. Such modifications include, but are not limited to, endonuclease digestion, mutations that create or destroy translation, initiation, and/or termination sequences, or that create variations in the coding region, or any combination thereof. Any technique for mutagenesis known in the art can be used, including, but not limited to, exposure to a mutagenic agent, such as radiation or a chemical mutagen, or in vitro site-directed mutagenesis (see, e.g., Hutchinson, et al., 1978, J. Biol. Chem. 253:6551).

As a result of alterations at the gene level, the expressed polypeptide may contain changes, e.g., deletions, additions or substitutions in amino acids, compared to the native molecule, which changes may result in one or more silent changes within the sequence to produce an immunogenic variant. For example, one or more amino acids of the native polypeptide can be conservatively substituted with an amino acid residue of similar charge, size or polarity, with the resulting polypeptide retaining its immunogenicity. Rules for making such substitutions are known in the art, and include, e.g., those described by Dayhof, M. D., 1978, Nat. Biomed. Res. Found., Washington, D.C., Vol. 5, Sup. 3.

Manipulation of the BHV-1 subunit component may also be made at the protein level. Any of numerous chemical modifications may be carried out by known techniques including, but not limited to: substitution of one or more L-amino acids of the native BHV-1 subunit component with corresponding D-amino acids, amino acid analogs, or amino acid mimics, so as to produce, e.g., carbazates or tertiary centers; or specific chemical modification as, e.g., with cyanogen bromide, trypsin, chymotrypsin, papain, V8 protease, $NaBH_4$, acetylation, formylation, oxidation, reduction, or metabolic synthesis in the presence of tunicamycin, etc.

A BHV-1 subunit component, or a fragment thereof, may be derivatized by conjugation of one or more types of chemical groups thereto, including but not limited to acetyl groups, glycosyl groups, lipids, and phosphates, or by conjugation to other BHV-1 subunit components, other proteins, polyamino acids (e.g., polylysine), polysaccharides, (e.g., sepharose, agarose, or cellulose), serum albumins, keyhole limpet hemocyanin, or commercially activated BSA, among others, using known techniques. Such conjugation is preferably by covalent linkage at amino acid side chains and/or at the N-terminus or C-terminus of the polypeptide. Methods for carrying out such conjugation reactions are well-known in the field of protein chemistry.

Derivatives useful in practicing the claimed invention also include those in which a water-soluble polymer such as, e.g., polyethylene glycol, is conjugated to the BHV-1 subunit component, or to a fragment or derivative thereof, to provide additional desirable properties while retaining, at least in part, the immunogenicity of the encapsulated subunit component. These additional desirable properties include, e.g., increased solubility in aqueous solutions, increased stability in storage, increased resistance to proteolytic degradation, and increased in vivo half-life. Water-soluble polymers suitable for conjugation to the BHV-1 subunit component include, but are not limited to, polyethylene glycol homopolymers, polypropylene glycol homopolymers, copolymers of ethylene glycol with propylene glycol, polyoxyethylated polyols, etc. Methods of making water-soluble polymer conjugates of proteins are known in the art, and are described, among other places, in U.S. Pat. No. 4,179,337; U.S. Pat. No. 4,609,546; U.S. Pat. No. 4,261,973; U.S. Pat. No. 4,055,645; and U.S. Pat. No. 4,415,665, which patents are incorporated herein by reference.

Fragments and derivatives of the BHV-1 subunit component that are useful in practicing the claimed invention are those that are capable of inducing a protective response against BHV-1 in a member of a bovine species when administered in encapsulated form according to the present invention. Such fragments and derivatives, once prepared, can be identified using nothing more than routine screening procedures known in the art. For example, a test fragment or derivative can be prepared and encapsulated as described herein, administered to a member of a bovine species, and the animal tested for seroconversion, e.g., by testing for the presence of virus-neutralizing antibodies in the serum, or for the ability of the vaccinated animal to resist subsequent challenge with BHV-1. Such methods for administering and screening are well-known in the art.

Microencapsulation of the Immunogen:

The Lewis salt-walled aqueous-cored microcapsules of the present invention are prepared as described below. The capsular membrane is an ionically-stabilized, anisotropic Lewis salt membrane. The encapsulation system employs the essentially instantaneous reaction between immunogenic composition-containing droplets of aqueous solutions of anionic polymers and low molecular weight cationic amine reactants, or between their water-soluble salts, to form water-insoluble films around the droplets and the immunogenic composition.

An aqueous solution or suspension of an immunogenic composition is dissolved or suspended in an aqueous solution of a suitable poly-anionic macromolecule (i.e., polymer), e.g., alginic acid. The resulting solution/suspension is then dispersed as droplets in an aqueous solution of a suitable water-soluble amine, e.g., spermine. Alternatively, this reaction can be carried out using water-soluble, neutral salts of the anionic polymer and water-soluble, neutral salts of the amine. At the apparent interface of the polymer droplets and amine solution, a salt exchange reaction takes place that results in the formation of a very poorly soluble salt (formed between the amine and polymer) which precipitates to form more or less spherical beads or capsules in which the immunogenic composition is captured. The resulting suspension of microcapsules containing encased immunogenic composition is then collected.

The anionic polymer and reactant amine are chosen from groups which, on reaction with one another, will rapidly form a poorly soluble precipitate and so encase the droplets before the polymer in the droplets diffuses sufficiently to distort appreciably the shape of the droplet or to lower the polymeric reactant concentration below that required to form a film. Thus, it is not necessary to employ polymer solutions of high viscosity, but it is necessary that the amine be capable of rapid diffusion to, and reaction at, the pseudophase boundary defined by the polymer droplet. The viscosity of the polymer solution may be as low as 2.5 to 10 centipoise.

A convenient means of dispersing the polymer solution droplets (comprising a solution or suspension of immunogenic composition in the polymer solution) in the amine solution is to allow an aerosol of the polymer solution to fall onto/into the amine solution as it is stirred. Use of a Bernoulli type nebulizer to generate the aerosol results in microcapsules with a relatively wide (Gaussian) distribution of particle sizes about the mean (with coefficients of variation approximating 10 to 20%). If narrower size distributions are desired, an acoustically-pulsed droplet generator as described herein may be used to provide highly uniform microcapsules (with coefficients of variability of diameter approximating 5%).

In some instances, as when acid labile immunogenic compositions are to be administered orally, it may be desirable to coat the microcapsules with an enteric material to protect them from gastric acid. Suitable enteric coating materials include cellulose acetate phthalate and polyoxyethylene crosslinked polymethacrylic acid. The technology for providing enteric coatings for small particles, tablets and capsules is well known in the pharmaceutical industry.

The reactants employed in preparing microcapsules from entirely aqueous solutions are available from a number of commercial vendors, but all described herein have been purchased from Fisher Scientific Company, F.M.C. Corporation, Ruger Chemical Company, Sigma Chemical Company, and/or The Upjohn Company.

Rapid release of encapsulated materials is accomplished by adding to an aqueous suspension of the microcapsules a water-soluble salt, either as a solid or as a solution of such salt. In either case, the salt employed must be capable of reacting with the insoluble film to yield water-soluble ionic products in a manner analogous to the reverse of the film-forming reaction. It is evident that the film-forming reaction is a reversible reaction. Slow release of soluble small molecules is realized through their gradual diffusion through the microcapsular walls. Diffusion rates depend on the size and solubility of the diffusing species and on the thickness and density of the capsular wall. Thus, in addition to providing a rapid release when wanted, the encapsulation process may be employed to provide controlled slow release of soluble encapsulated materials.

Anionic polymers or macromolecules which have been shown to be useful as encapsulating reagents are drawn from the group of water-soluble polymers with reactive carboxylate or sulfate groups consisting of alginic acids, alginic acids linked to fluorophores such as fluorescein isothiocyanate or rhodamine isothiocyanate, arabic acid, cellulose sulfate, carboxymethylcellulose, carrageenans, chondroitin sulfate, heparin, polyacrylic acid, polyoxyethylene crosslinked polyacrylic acid (e.g., EUDRAGIT L-100®, produced by Rohm Pharma) and polyvinylcarboxylic acid (e.g., CARBOPOL 934®). In some preferred embodiments, the anionic polymer is selected from the group consisting of alginic acid (Fisher Scientific Co., Fairlawn, N.J.), polyacrylic acid (Aldrich Chemical Co., St. Louis, Mo.), cellulose sulfate (Aldrich Chemical Co., St. Louis, Mo.), cellulose acetate phthalate (Eastman Organic Chemicals, Rochester, N.Y.), Carbomer USP (CARBOPOL 934® polyvinylcarbpoxylic acid, B.F. Goodrich, Cleveland, Ohio), carboxymethylcellulose USP (medium viscosity, Ruger Chemical Co. Inc., Irvington, N.J.), Heparin USP (The Upjohn Co., Kalamazoo, Mich.), and arabic acid (isolated according to the method described in U.S. Pat. No. 2,666,759 which is incorporated herein by reference), each of which is provided as a sodium salt. It is generally preferred that the anionic polymers be employed as their neutral salts with an alkali metal ion, e.g., sodium or potassium, or with ammonium or a trialkanolamine, e.g., triethanolamine, among others. In some preferred embodiments, the anionic polymer is alginic acid provided in its neutral salt form as sodium alginate.

Cationic reactants useful in preparing microcapsules according to this invention are drawn from the group of mono-, di-, tri- and tetra-amino compounds which includes: arginine, decylamine, dodecylamine, ethylenediamine, piperazine, methylene blue, octadecylamine, triethylamine, triethyltetramine, and spermine. In some preferred embodiments, the amine is selected from the group consisting of arginine (Sigma Chemical Co., St. Louis, Mo.), piperazine (Sigma Chemical Co., St. Louis, Mo.), ethylenediamine (Aldrich Chemical Co., St. Louis, Mo.), triethylamine (Aldrich Chemical Co., St. Louis, Mo.), triethylenetetraamine (Aldrich Chemical Co., St. Louis, Mo.), methylene blue (Fisher Scientific Co., Fairlawn, N.J.), and spermine, each of which may be provided as a hydrochloride salt, and octadecylamine (Sigma Chemical Co., St. Louis, Mo.) which may be provided as an acetate. It is generally preferred that the amine is provided as a halide salt, e.g., chloride, bromide, or iodide, or as a low molecular weight alkanoic salt, e.g., having 6 carbon atoms or less, or that is soluble to at least 1% by weight in water, including e.g., an acetate, propionate or cyclopropionate salt, among others. In some preferred embodiments, the amine is spermine provided in its neutral salt form as spermine hydrochloride.

Prior to formation of microcapsules with captured immunogenic compositions, the anionic polymers and amines may be tested individually to determine their effect on immunogenicity of immunogenic composition. In order to determine the effect of anionic polymers and amines on immunogenicity, one having ordinary skill in the art can perform routine assays using readily available starting materials. For example, the ability of a selected immunogenic peptide or protein to invoke an immune response may be determined in the presence of various concentrations of the component being evaluated to ascertain the effect the component has on the immunogenicity of the peptide or protein.

Since in some embodiments it is preferred that the microencapsulated vaccine be effective when administered orally, the anionic polymers and amines which do not inactivate the immunogenic composition are tested in combination to determine their capacity to form microcapsules that resist breakdown in simulated gastric acid.

The aqueous sodium salt of anionic polymer, preferably 1 ml, is added dropwise to aqueous amine hydrochloride (or acetate), preferably 1 ml, to determine the capacity to form an interfacial precipitate. Combinations which generate solid material are used to make microcapsules. Microcapsules are formed by dispersion of the sodium salt of anionic polymer as droplets approximately 5 pm in size into an aqueous solution of the amine salt in a manner analogous to that described for preparing calcium alginate microcapsules in U.S. Pat. No. 4,744,933, which is incorporated herein by reference. Short-term stability of microcapsules can be tested by observation at room temperature for 5 days in aqueous solution. Microcapsules stable at room temperature can be treated with simulated gastric acid (pH 1.2) at 37° C. for 2 hours.

The combinations of anionic polymers and amines which do not inactivate the immunogenic composition, and which provide stable microcapsules, are then used to form microencapsulated vaccines. The immunogenic composition is first combined with the anionic polymer. The polymer/immunogenic composition mixture is then dispersed as droplets into amine.

Microcapsules according to the present invention may be made with the apparatus described below, which allows preparation of microcapsules of extremely narrow size distribution at selectable median sizes. This is important in making microcapsules intended for injection, or for uptake through the gut-associated lymphatic tissues (a subset of which are often referred to as Peyer's patches) or the bronchus-associated lymphatic tissue of the respiratory system. Microcapsules intended for intravenous injection must necessarily be less than about 5 microns in diameter, small enough to pass through capillary beds. For administration by inhalation, particles must be in the respirable size range, i.e., less than about 5 microns, while to reach deep alveolar sites it is preferred that particles be in the size range below 2 microns. The tissues of Peyer's patches are highly discriminatory in the size of particles which they will engulf, selecting only particles less than 10 microns and preferably about 5 microns in size. The device described below can produce populations of microcapsules of various sizes, with standard deviation from the mean of less than 0.25 micron in the range near the mean volume diameter of 5 microns.

Microcapsule Forming Reactions:

In accordance with the present invention, one of two types of reactions can be employed to form the microcapsules in aqueous media. These are acid-base reactions and salt exchange reactions.

Acid-base Reaction:

Several water-soluble acidic polymers will react in aqueous solution with low molecular weight water-soluble mono- or oligo-amines to form poorly water-soluble salts which may precipitate. The group of water-soluble acidic polymers which participate in this reaction includes arabic acid, cellulose sulfate, chondroitin sulfate, heparin, and fluorescent derivatives of the above acidic polymers. The group of amines which yield poorly water-soluble salts in this reaction includes arginine, decylamine, dodecylamine, ethylenediamine, hexadecylamine, methylene blue, octadecylamine, piperazine, spermine, tetradecylamine, triethylamine and triethylenetetramine.

Salt Exchange Reaction:

A similar reaction occurs with formation of poorly water-soluble salts if the acidic polymers described above or certain relatively poorly water-soluble acidic polymers are employed as solutions of their respective neutral salts (e.g., sodium, potassium, ammonium or triethanolamine, among others), and the amines described above are dissolved as their water-soluble salts (e.g., hydrochloride, hydrobromide, acetate, or propionate, among others). The similar reaction may be considered a salt exchange reaction in which one of the products (e.g., sodium chloride or sodium acetate) is soluble and the amine-polymer salt is poorly soluble. The group of acidic polymers useful as their water-soluble salts in the salt-exchange reaction includes those polymers named above and also the following acidic polymers in the form of their sodium or other water-soluble salts: alginic acid and fluorescent derivatives, e.g., fluorescein isothiocyanate and rhodamine isothiocyanate, derivatives of alginic and other acids, carboxymethylcellulose, cellulose acetate phthalate, EUDRAGIT L-1009 (polyoxyethylene crosslinked polyacrylic acid), polyacrylic acid, polyvinylacrylic acid and fluorescent derivatives of these polymers. This larger group of acidic polymers will all react as their sodium or other water-soluble salt with at least one of the members of the group of amines in the form of their hydrochloride or acetate salts to form poorly water-soluble amine-polymer salts in the salt exchange reaction. However, not all combinations that form poorly soluble salts will form microcapsules in accordance with this invention. See the test described below and compare FIGS. 2 and 3.

As used herein, the terms "anionic polymer", "polymer strand" and "anionic polymer solution" are meant to refer to polymers which participate in forming the amine-polymer salt. References to concurrently formed water-soluble products of the exchange reaction (e.g., sodium chloride or sodium acetate) are not expressly referred to herein unless there is specific need to refer to these water-soluble products.

Thus, the group of anionic polymers that can be used as microcapsule-forming agents in accordance with this invention consists of polymeric substances with carboxylate acidic functional groups (alginic, arabic, carboxymethylcellulose, EUDRAGIT L-100® polyoxyethylene/crosslinked polyacrylic acid polyacrylic acid and polyvinylcarboxylic acid), sulfate acidic groups (carrageenans, cellulose sulfate, chondroitin sulfate, heparin), linear or branched polyalkylene backbones (polyacrylic acid, poly-vinylcarboxylic acid), linear carbohydrate backbones (alginic acid, cellulose sulfate, chondroitin sulfate, heparin) and branched carbohydrate backbones (arabic acid).

In the microcapsules of the present invention, the anionic polymer constitutes the major structural component of the microcapsular walls. Typically, the polymer is chosen to provide a desired range of spacing between nearest neighbor anionic groups. Thus, in their extended forms above the theta temperatures of the polymers, the interanionic distances approximate the equivalent of 2 methylene groups in poly-acrylic acid, 6 in alginic acid, cellulose sulfate, chondroitin sulfate, and heparin, 10 in carboxymethylcellulose and between 20 and 30 in highly branched arabic acid. This allows one to selectively form capsule walls having different porosities. See U.S. Pat. No. 3,959,457 to Speaker et at. (esp. col. 5, I. 6–20).

Because all the anionic polymers used in the present invention have average molecular weights well above 10 kD, they are multivalent and can react with the amines in a wide range of stoichiometries. In practice it has been found that the preferred range of stoichiometries of amine to anionic polymer repeat unit is about 0.2 to about 0.6. In other words, about 2 to 6 amine molecules are available to combine with each 10 anionic groups on the polymers, to form salts of the polymer. Furthermore, because several of the amines are also multivalent, the reacting species can, in theory, form complex networks in which the amines serve to crosslink anionic polymer strands. The precipitates, which form essentially instantaneously when solutions of anionic polymers and amines are stirred together, tend to be amorphous, cohesive, adhesive and often filamentous. However, not all combinations of anionic polymer and amine yield poorly soluble amine-polymer salt. FIG. 2 lists two groups of reactive species tested to date and indicates the combinations which have been successful in forming precipitates when these combinations were allowed to react. The anionic polymers and amines are listed in order of increasing approximate equivalent weights (shown in parentheses) of the amines and polymer repeating units.

Although the majority of the combinations of anionic polymer and amine will react to form a poorly water-soluble amine polymer salt, a smaller subset of this set appears to be capable of forming microcapsules, at least under the conditions tested to date. Thus, the simple ability to form a water-insoluble amine polymer salt does not in itself provide definitive identification of microcapsule wall-forming components, at least under the conditions tested to date.

To determine whether an amine/polymer pair will form capsules and microcapsules, the following procedure is useful. Prepare separate aqueous solutions of the amine and polymer, containing about 1% w/v of the acid form of the polymer and an approximately stoichiometrically equivalent amount of amine, in equal volumes of water. Alternatively, if the polymer or amine are not soluble to such an extent, prepare separate solutions of water-soluble salts of the amine (e.g., hydrochloride or acetate) and of the polymer (e.g., sodium or ammonium). To an approximately 5 ml volume of the amine solution add successive 20 to 25 microliter volumes of the polymer solution, delivering the polymer solution dropwise from a height of about 1 centimeter. Visually observe the two solutions as the one is added to the other. Note whether the droplets of polymer solution merge with the amine solution and the system becomes homogeneous or whether a pellicle forms about the polymer solution droplets and keeps them as physically distinct and mechanically separate entities.

If the added droplets form such a pellicle and do not blend with the amine solution to make a homogeneous solution, it is probable the reactant pair can be used to make microcapsules. To test this probability more closely, it is necessary to repeat the experiment using polymer droplets and amine solutions prepared over a range of concentrations to establish optimal reactant concentrations.

If either the amine or acid form of the polymer is inadequately soluble to conduct the test as described above, the salt forms of the reactant pair may be used together in their place.

FIG. 3 indicates which amine polymer salts have effectively formed stable microcapsules, under conditions tested to date.

The ability of a combination of aqueous solutions of amine and polymer to form a stable microcapsular configuration requires first that the reactants be water-soluble and oppositely charged in order that they may combine to form a poorly soluble salt. Importantly, the anionic polymer strands in solution must not rapidly diffuse compared to the ability of the amine molecules (ions) to diffuse. Further, it is preferred that the droplets of anionic polymer solution be introduced into the amine solution in such a manner that the polymer droplets do not become extensively distorted or very rapidly mixed with the bulk of the amine solution. These several requirements are relatively easily met. The basis for these requirements may be understood in terms of the steps in the process described in greater detail below.

At the start of the microcapsule-making process, the aqueous solutions of anionic polymer and of the amine are mechanically (i.e., physically) separated phases. At room temperature, the water molecules of the anionic polymer solution are expected to have high (0.9+) thermodynamic activity coefficients and to diffuse far more rapidly than do the polymer molecules. The polymer strands (molecular weights above 10 kD, 100,000 AMU) are of colloidal size and can be expected to behave as do other colloidal particles. In particular, it is expected that a colloidal solution of anionic polymer will tend to structural inhomogeneity with development of microregions of relatively high colloidal polymer concentration and others void of polymer. This behavior of colloidal polymers has recently been shown by Ito et al., 1994, Science 263:66–68, with time lapse confocal laser micrographs. The micrographs show such tendency toward inhomogeneity and void structure. Ito et al. discuss this behavior in terms of ionic polymers such as those employed in this invention (e.g., sodium polyacrylate). By contrast, amine reactants (molecular weights less than 400) are thermodynamically far more active than are the anionic polymer strands, diffuse far more rapidly than do the polymer strands (but more slowly than do water molecules), and are understood to be homogeneously distributed throughout their solutions.

When a droplet of anionic polymer solution is introduced into a bulk volume of amine solution it is expected that the previously separate aqueous phases will essentially instantaneously combine to form a single continuous aqueous phase with no discernible phase boundary for the previously separate aqueous components. On the other hand, the low diffusion coefficients of the anionic polymers (typically less than $7 \times 10^{-7}$ cm$^2$/sec for colloidal polymers in the mass range near 10 kD) limit movement of polymer molecules from their initial positions relative to the remainder of the polymer solution droplet and allow time for a multiplicity of amine molecules (ions), moving nearly as rapidly as water molecules, to come into proximity with the polymers, to be electrostatically attracted to them, and to form salts with anionic groups of the polymers. Thus, the relative immobility of the polymer molecules during reaction with numerous amine units allows precipitation of a shell which conforms to the approximate initial positions of the polymer strands and retains the shape of the droplet.

The development of this shell around a droplet may be easily observed macroscopically by carefully adding an approximately 20 microliter, approximately spherical droplet of aqueous 1% w/v sodium carboxymethylcellulose solution to an approximately 1% w/v aqueous solution of decylamine hydrochloride. Within a small fraction of a second, a barely discernible spherical pellicle forms around the added droplet and, during a few more seconds, the pellicle becomes increasingly thicker and more opalescent. The resulting microcapsule can be retrieved with a Pasteur pipette or collected on fine netting. It should be noted that, if such a polymer droplet is delivered to the amine solution from a height of several centimeters, it is highly probable that the droplet may be distorted to form an oblate spheroid or biconcave disk-like structure which similarly gradually becomes thicker and more opalescent of shell. If the amine solution is stirred or rapidly flowing, added droplets tend to form prolate spheroids or filamentous particles which similarly thicken. If the droplets of polymer solution are smaller, they may be dispersed onto or into the amine solution from greater heights or onto/into flowing amine solution with less distortion. In practice, droplets of approximately 5 to 7 micron diameter may be applied from a height of 5 centimeters to the surface of an amine solution flowing at linear velocity of about 1 centimeter per second and still produce essentially spherical microcapsules.

While it is perhaps too simple to describe the process by which pellicles surrounding polymer droplets form and thicken to make microcapsules in terms only of diffusional processes, such a description conveys a fairly accurate sense of what happens. A more detailed understanding may be derived through the description of the mechanism and dynamics of ion transport across a liquid-liquid interface. Benjamin, I., 1993, *Science* 261:1558–1560, has shown that, although the time averaged water-dichloroethane interface is "molecularly sharp", over short time intervals, thermal fluctuations induce formation of capillary interdigitations of each liquid phase with the other. These capillary "fingers" allow ion transfer from one phase to another even though the bulk phases are clearly separate. It is to be expected that similar capillary intrusions of an amine-bearing part of the aqueous phase into polymer-bearing aqueous phase might similarly provide a mechanism by which the ions of the amine polymer salt might interact to develop a film or pellicle without grossly disturbing the integrity of the polymer droplet.

In effect, then, the ability of the reactant solutions to form discrete microcapsules depends at least in part on the relative immobility of polymer strands in aqueous media and the relatively much greater mobility of amine molecules (ions), and perhaps also in part on the brief thermally induced fluctuation of the apparent interfacial boundary between amine and polymer solutions. It does not require high viscosity solutions, but rather one species of slow diffusing reactant. This interpretation of the mechanism of microcapsule formation is quite at odds with the constraints on microcapsule formation put forth in other entirely aqueous encapsulation systems.

The reaction leading to formation of amine polymer salt precipitates may be seen to be a simple salt exchange and as such has the characteristics of a reversible reaction. That this is so is demonstrable by adding an excess of the soluble salt formed in the reaction, or a concentrated solution of it (e.g., sodium chloride or sodium acetate), to a suspension of microcapsules. Raising the concentration of sodium chloride in the aqueous medium surrounding a population of microcapsules to about 4% w/v generally results in their rapid dissolution. However, treatment with sodium chloride or another electrolyte capable of yielding soluble polymer and amine salts (e.g., sodium phosphate to make a 4% w/v solution) may not completely disrupt microcapsules made with very poorly soluble amines (e.g., hexadecylamine, octadecylamine), and, to disrupt such microcapsules, e.g., for analytical purposes, it is useful to add a solvent that is able to deplete the aqueous concentration of amine (e.g., cyclohexane).

A presently preferred method for forming the microcapsules of the invention is to employ an acoustical droplet-forming device that has been developed for this purpose. This device produces a stream of uniform fine droplets of anionic polymer solution and directs them onto and through a constantly renewed surface of the cationic reactant solution (amine) so that newly arriving droplets do not impinge on earlier delivered droplets. The device thereby (1) reduces the tendency to form microcapsule agglomerates and (2) provides a means to produce large populations of microcapsules with a very narrow size distribution range. The machine operates by sonically pulsing a downward flowing vertical stream of polymer solution just before it emerges from a narrow orifice so that the sound wave propagating through the liquid stream initiates a series of constrictions in the stream which then, under the influence of the surface tension of the liquid, causes the stream to break up into a train of uniform droplets. The droplet train is directed coaxially into a narrow cylindrical tube which is supplied through a side opening (or its topologic equivalent) with a continuous flow of the cationic reactant. Thus, each newly arriving polymer droplet encounters a fresh surface of cationic reactant and has minimal opportunity to strike and coalesce with another polymer droplet before it begins to form its own capsular wall and exits the lower end of the tube.

The major components of the acoustic device for preparation of microcapsules may perhaps be best described in terms of its functional sequence as it brings two liquid streams together to form microcapsules. In this device, aqueous solutions of anionic polymer and amine (or their corresponding neutral salts) are stored in separate reservoirs and pumped through separate transfer lines. The amine solution is fed to and enters the stem of a modified T-tube which serves as the primary reaction vessel. The T-tube is mounted so that the cylindrical axis of the bar of the T is oriented vertically. Amine solution entering the stem of the T-tube flows horizontally for a few millimeters before it flows by gravity out the lower half of the T-tube bar. (In practice, it has been useful to employ not a simple T-tube but rather one of the sort often referred to in clinical chemical laboratories as a "cactus tube". A cactus tube has the general shape of the lower case letter h and, in this application, the tube is positioned so that the h shape is upside down. The straight part of the cactus tube is about 2 cm long and has an internal diameter of about 2 mm.) Amine solution flowing from the T-tube may be returned to the reservoir and recirculated.

The polymer solution is pumped through a membrane filter (of 8 micron or finer retentiveness), then through a glass capillary, the distal end of which is constricted to a nominal diameter of 20 to 25 microns, and emerges in the form of a fine continuous liquid jet. (The constricted capillary is readily fabricated from a volumetric 25, 50 or 100 microliter glass capillary tube of a type generally available from laboratory supply houses, e.g., A. H. Thomas Co.) The constriction is preferably such that the jet of polymer solution emerges with a velocity in the range between 4 and 5 meters per second when the polymer solution is pumped at 1 to 2 ml per minute, but flow rates and velocities outside these ranges may, of course, be employed.

The capillary is aligned in a shallow V-shaped groove in a metal block and tightly held by compression springs against the axially vibrating end of an acoustic transducer (e.g., of a laboratory ultrasonic probe operated at a nominal energy output of 40 watts) so that acoustic energy is transferred through the wall of the capillary to the flowing polymer solution, causing the jet of polymer solution to break up into a train of droplets of uniform size.

The transducer-capillary-compression block assembly is positioned so that the emerging train of polymer solution droplets passes through air for about 3 cm and is directed axially into the upper end of the T-tube bar to impinge on the amine solution entering from the side (stem) of the T-tube. The polymer solution droplets react with the amine solution to form microcapsules that flow with the amine solution out the lower end of the T-tube bar.

Even in the absence of sonic stimulation, the jet of polymer solution which emerges from the capillary constriction, as described above, would normally spontaneously break up into a train of droplets of varying size as a result of varying natural instabilities of the fluid stream and of the atmosphere into which the jet emerges, the so-called Rayleigh disruption of a liquid jet. However, it is desirable that droplets of uniform size be produced in order to make microcapsules of uniform size. It is for this reason that, in accordance with the preferred embodiment of this invention, droplets of uniform size are produced by periodically sonically disturbing the liquid stream to initiate a train of sufficiently strong compression (sound) waves along the axis of the jet. The train of sound waves moves through the liquid medium and away from the orifice far more rapidly than the liquid itself. (The jet emerges at a velocity of 4 to 5 meters per second.) Propagation of the wave train along the length of the jet establishes an interference pattern of increasing constructive amplitude at successive nodes along the path of the jet. At some distance from the orifice, the amplitude of the surface wave becomes greater than the surface tension of the liquid, and droplets of polymer solution form at the sonicator frequency. The generation of a train of droplets of uniform size in this manner is reported in some detail by Galley, P. J., and Hieftje, G. M., 1992, *Applied Spectroscopy* 45:1460–1463.

To illustrate the foregoing method and apparatus, reference is made to the accompanying FIG. 4, in which is shown "h" shaped tubular member 10, including a side-leg entry segment 14 and a vertical intersecting segment 12, through which the amine solution 16 is pumped downwardly at the upper end of tube segment 14 so that it enters upright segment 12 and is diverted at the intersection of segment 14 and segment 12 into a downwardly flowing portion from which it exits at the bottom end of tubular segment 12. Above the intersection of segments of 14 and 12, the polymer solution 22 is introduced through a capillary member 18, the bottom end of which is spaced a predetermined distance (about 3 centimeters in the exemplary description above) above the intersection of segments of 14 and 12, at which the flow of the amine solution is diverted downwardly, so that drop-wise disposed portions of polymer solution 22 are combined with the downwardly-flowing amine solution at that point.

As described above, to enhance the uniformity of the drop-wise, downwardly-flowing portions 22 of polymer solution, capillary tube 18 is rigidly held in a metal block 24, with a V-groove holding slot (not shown in the figure) and acoustically stimulated intermittently. For that purpose, an acoustic probe 20 is in contact with capillary tube 18 near the lower end thereof.

One may estimate the numbers of individual droplets produced per unit time from the frequency of the sonicator. In most instances, a sonicator with a frequency of 20 kHz was employed. The estimate of the number of droplets formed may be slightly in error due to instances in which successive droplets may impinge on one another and coalesce or adhere to one another to form aggregated microcapsules. In practice, far less than 1% of the droplets occur as fused or coalesced forms. Assuming all droplets are formed separately, one may calculate the size of individual droplets from a knowledge of polymer flow rate. At a nominal anionic polymer flow rate of 1 ml per minute, the volume of individual droplets is 0.05 microliters (cubic millimeters), 3 corresponding to a spherical droplet diameter of 4.57 microns. The diameter of microcapsules formed at flow rates near 1 ml per minute and acoustic frequencies of 20 kHz is approximately 5 microns as estimated from volume diameter sizing (Coulter principle).

Alternatively, droplets of the polymer solution of essentially any size may be introduced into the cationic reactant solution (e.g., by spraying, or by dropwise dispensing from a pipette) to form microcapsules. In many applications it is desirable that the microcapsules formed be of highly uniform size, and thus some means of inducing this uniformity, such as the acoustic method described above, is preferred. Such applications include delivery to the lymphatic tissues of the intestine, often referred to as Peyer's patches. The M cells of Peyer's patches preferentially reject particles larger than about 10 microns, but engulf particles in the size range below about 10 microns and transfer them to other lymphatic cells.

In general, the microcapsules of the present invention may range in size from 0.1 to 2,000 microns. A preferred size range, useful for general oral administration, is from 500 to 1,000 microns. In some embodiments, the range is from 100 to 200 microns. In other embodiments, such as in the administration of substances intended for delivery to Peyer's patches in the lymphatic tissue of the intestine, a particularly preferred size range is from 1 to 10 microns.

Depending in part on the degree to which manufacturing fluid is removed and in part on the nature of the core solute, the aqueous core microcapsules may be collected as a free-flowing suspension, a viscid flowable concentrate, a paste, a friable flake or, with further treatment, as a lyocake. Lyophilization is particularly desired to provide stable microcapsules with highly water-soluble core materials.

Once encapsulated, immunogenic compositions are protected from the environment, but may be slowly released from the microcapsules by suspending the capsules in an aqueous medium into which the immunogenic compositions can actively diffuse through the semi-permeable microcapsule walls. In general, where the nature of the wall-forming reactants is held constant, highly water-soluble immunogenic compositions are observed to be released more rapidly than are poorly water-soluble immunogenic compositions and, in general, immunogenic compositions of low molecular weight are released more rapidly than are those of higher molecular weight. In some embodiments, conversion of the microcapsules to lyocakes and resuspension in aqueous media is preferred.

Vaccines:

Vaccines according to the invention comprise at least one microencapsulated immunogenic composition and a pharmaceutically or veterinarily acceptable carrier or diluent. Optionally, the vaccine may comprise additional components, including microencapsulated and non-encapsulated immunogenic compositions and/or adjuvants.

Thus, the present invention provides a vaccine for protecting a member of a bovine species against BHV-1, comprising an immunogenic amount of microcapsules comprising an anisotropic Lewis salt membrane encapsulating an aqueous or substantially aqueous core and an immunogenic composition surrounded by the salt membrane, said microcapsules being substantially free of non-aqueous contaminants, said salt membrane comprising a precipitate resulting from the interfacial reaction of a selected water-soluble anionic polymer with a selected water-soluble amine, or the interfacial reaction of a water-soluble neutral salt of a selected anionic polymer with a water-soluble neutral salt of a selected amine. In a preferred embodiment, the selected anionic polymer is alginic acid, which is preferably in the form of a corresponding water-soluble, neutral salt (e.g., sodium alginate), and the selected amine is spermine, which is preferably in the form of a corresponding water-soluble, neutral salt (e.g., spermine hydrochloride).

The immunogenic composition comprises a subunit component of BHV-1 which is capable of inducing a protective response against BHV-1 when administered in encapsulated form according to the present invention to a member of a bovine species. In a preferred embodiment, the subunit component of the immunogenic composition of the vaccine comprises a BHV-1 glycoprotein such as, e.g., gI, gIII or gIV, or an immunogenic fragment or derivative thereof. In a more preferred embodiment, the immunogenic composition of the vaccine comprises a truncated BHV-1 glycoprotein, such as, e.g., BHV-1-gD. In a more preferred embodiment, the immunogenic composition of the vaccine is BHV-1-gD. The vaccine may further comprise a pharmaceutically or veterinarily acceptable carrier or diluent, and, optionally, an adjuvant. As used herein, the term "member of a bovine species" refers to cows and oxen.

The phrase "capable of inducing a protective response" is used broadly herein to include the induction of any immune-based response in the animal in response to vaccination, including either an antibody or cell-mediated immune response, or both, that protects the vaccinate against BHV-1. The term "protective response" as used herein is not limited to absolute prevention of infection by BHV-1, but is intended to include any reduction in infectivity of the virus, or in the severity of a disease or condition normally resulting from infection with BHV-1, including a detectable reduction in one or more of the pathological effects or symptoms normally resulting from infection, or a detectable reduction in the rate of progression of one or more of such pathological effects or symptoms, compared to an unvaccinated, infected animal.

Vaccines of the present invention may be formulated following accepted convention using standard buffers, carriers, stabilizers, diluents, preservatives, and solubilizers, and may also be formulated to facilitate sustained release. Diluents may include water, saline, dextrose, ethanol, glycerol, and the like. Additives for isotonicity may include sodium chloride, dextrose, mannitol, sorbitol, and lactose, among others. Stabilizers include albumin, among others. Adjuvants may be employed, examples of which include the RIBI adjuvant system (Ribi Inc.), alum, aluminum hydroxide gel, oil-in-water emulsions, water-in-oil emulsions such as, e.g., Freund's complete adjuvant and Freund's incomplete adjuvant, Block co polymer (CytRx, Atlanta GA), QS-21 saponin adjuvant (Cambridge Biotech Inc., Cambridge Mass.), SAF-M threonyl-MDP adjuvant (Chiron, Emeryville Calif.), AMPHIGENO adjuvant, Quil A, monophosphoryl lipid A, and Avridine lipid-amine adjuvant. The vaccine may further comprise one or more other immunomodulatory agents such as, e.g., interleukin-1 or other known cytokines. Suitable other vaccine vehicles, carriers and additives are known, or will be apparent to those skilled in the art. See, e.g., *Remington's Pharmaceutical Science*, 18th Ed., 1990, Mack Publishing, which is incorporated herein by reference. Vaccines may be maintained in solution or lyophilized. Lyophilized vaccine may be stored conveniently and reconstituted with a sterile diluent solution prior to administration.

The amount of microencapsulated immunogenic composition administered to the animal depends upon such factors as the nature of the immunogenic composition, the species, age, weight, and general physical characteristics of the animal being vaccinated, and the composition of the vaccine. Determination of optimum dosage for each parameter may be made by routine methods in view, e.g., of published studies. Specifically regarding administration of microencapsulated subunit components of BHV-1, and, in particular, microencapsulated BHV-1-gD, the amount administered to a member of a bovine species will preferably range from about 100 pg to about 150 $\mu$g of BHV-1-gD, more preferably from about 250 pg to about 100 $\mu$g, and most preferably from about 400 pg to about 60 $\mu$g. The typical dose volume of the vaccine will range from about 0.5 ml to about 5 ml per dose per animal.

The vaccine regimen may also be selected based on the above-described factors. Animals may be vaccinated at any time, including at weaning age or younger, or just prior to or at the time of breeding, or at the time at which onset of infection in a herd is first detected. Supplemental administrations, or boosters, may be required for full protection. One method of determining whether adequate immune protection has been achieved is to determine seroconversion. This and other methods for determining whether adequate immune protection has been achieved are well-known in the art.

The present invention also provides a method of vaccinating a member of a bovine species against BHV-1, comprising administering a vaccine comprising an immunogenic amount of the microcapsules of the present invention. Vaccines according to the invention may be administered by any appropriate route such as, e.g., by oral, intranasal, intramuscular, intraperitoneal, intravenous, intra-arterial, subcutaneous, rectal or vaginal administration, or by a combination of routes.

In addition, the present invention provides a kit for vaccinating a member of a bovine species against BHV-1, comprising a first container comprising an immunogenic amount of the microcapsules of the present invention. The kit further comprises a second container comprising a pharmaceutically or veterinarily acceptable carrier or diluent. The microcapsules of the kit may optionally be supplied in lyophilized form. The kit may also optionally comprise an adjuvant.

The present invention further provides a combination vaccine for protecting a member of a bovine species against BHV-1 and, optionally, another disease or pathological condition which afflicts a bovine species, which vaccine comprises an immunogenic amount of microcapsules comprising an anisotropic Lewis salt membrane encapsulating an aqueous or substantially aqueous core and a first immunogenic composition surrounded by the salt membrane, said microcapsules being substantially free of non-aqueous contaminants, said salt membrane comprising a precipitate resulting from the interfacial reaction of a selected water-soluble anionic polymer with a selected water-soluble amine, or the interfacial reaction of a water-soluble neutral salt of a selected anionic polymer with a water-soluble neutral salt of a selected amine. In a preferred embodiment, the selected anionic polymer is alginic acid, which is preferably in the form of a corresponding water-soluble, neutral salt (e.g., sodium alginate), and the selected amine is spermine, which is preferably in the form of a corresponding water-soluble, neutral salt (e.g., spermine hydrochloride).

The first immunogenic composition comprises a subunit component of BHV-1 capable of inducing a protective response against BHV-1 when administered in encapsulated form according to the present invention to a member of a bovine species. In a preferred embodiment, the first immunogenic composition comprises a BHV-1 glycoprotein such as, e.g., gI, gIII or gIV, or an immunogenic fragment or derivative thereof. In a more preferred embodiment, the first immunogenic composition comprises a truncated BHV-1 glycoprotein, such as, e.g., BHV-1-gD. In a more preferred embodiment, the immunogenic composition is BHV-1-gD.

The combination vaccine further comprises an immunogenic amount of a second immunogenic composition, which is selected based on its ability to induce a protective response against either BHV-1 or another disease or pathological condition which afflicts a bovine species, as known in the art. Any immunogenic composition known to be useful in a bovine vaccine composition may be used as the second immunogenic composition of the combination vaccine of the present invention. Such immunogenic compositions include but are not limited to those that provide protection against bovine respiratory syncitial virus, bovine viral diarrhea virus, parainfluenza virus types I, II, or III, Leptospira spp., Vibrio fetus, rotavirus, coronavirus, rabies, Pasteurella hemolytica, Pasteurella multocida, Clostridia spp., Tetanus toxoid, E. coli, and Neospora spp., among others. The second immunogenic composition of the combination vaccine may either be encapsulated by the method described herein, or by any other known method, or may remain non-encapsulated. If encapsulated, the second immunogenic composition may either be encapsulated in the same microcapsules with the BHV-1 subunit component, or may be encapsulated separately in a different set of microcapsules.

The immunogenic component of the second immunogenic composition may optionally be linked, covalently or otherwise, to the BHV-1 subunit component, or to an immunogenic fragment or derivative thereof, to produce a chimeric molecule. In one embodiment, the component of the second immunogenic composition comprises a hapten, the immunogenicity of which is detectably increased by conjugation to the BHV-1 subunit component of the first immunogenic composition.

Chimeric molecules comprising components of the first and second immunogenic compositions described above may be synthesized using one or more techniques known in the art. For example, a chimeric molecule may be produced synthetically using a commercially available peptide synthesizer utilizing standard chemical synthetic processes (see, e.g., Merrifield, 1985, Science 232:341–347). Alternatively, a chimeric molecule may be produced using recombinant DNA technology, as known in the art, whereby, e.g., nucleotide sequences encoding the different components of the chimeric molecule are spliced together in-frame and expressed in a suitable transformed host cell for subsequent isolation. Ample guidance for carrying out such recombinant techniques is provided in Maniatis, et al., 1989, supra; Ausubel, et al., 1989, supra; Sambrook, et al., 1989, supra; and Innis et al. (eds) 1995, supra, which have been incorporated herein by reference.

The combination vaccine may further comprise a pharmaceutically or veterinarily acceptable carrier or diluent, and, optionally, an adjuvant.

The following example is illustrative only, and does not limit the scope of the present invention.

EXAMPLE

The capacity of microencapsulation to enhance virus-specific immune responses to BHV-1-gD was determined. Also examined was the importance of both protein capture efficiencies and stability of captured proteins within microcapsules in enhancement of virus-specific immune responses.

Materials and Methods

Virus and Viral Proteins:

BHV-1-gD at a concentration of 696 µg per ml was provided by Pfizer Inc. Plasmid constructions, plasmid transfections, and expression, purification, and quantitation of BHV-1-gD were performed as described by van Drunen, S., et al., 1994, Vaccine 12:1295–1302, which is incorporated herein by reference.

Formation of Microcapsules:

Microencapsulation of BHV-1-gD using spermine-alginate or spermine-chondroitin sulfate was performed as follows. Separate aqueous 1% w/v solutions of high viscosity sodium alginate (Fisher Scientific Co., Fairlawn, N.J., or Kelco, Clark, N.J.), or sodium chondroitin sulfate C (Sigma Chemical Co., St. Louis, Mo.) were allowed to hydrate at refrigerator temperature overnight, and after hydration were passed through 8 micron mixed cellulose ester filters (Millipore, Bedford, Mass.). Volumes of 2.5 ml of vaccine and successive half volumes to 0.078 ml were transferred with the aid of a calibrated pipette to 0.6 ml volumes of 1% w/v sodium alginate solution and to 5 ml volumes of sodium chondroitin sulfate solution in separate vessels. Each vaccine-polymer mixture was diluted to 10 ml, mixed by vortexing and, using the previously taught acoustical droplet-forming device, instilled as a stream of uniform fine droplets into separate 40 ml volumes of aqueous 0.125% w/v spermine (Sigma Chemical Co., St. Louis, Mo.) adjusted to pH 7.0±0.1 with hydrochloric acid.

In order to minimize the opportunity for polymer droplets entering the spermine hydrochloride solution in the cactus tube to impact upon nascent capsules, the spermine hydrochloride solution was delivered to the cactus tube at a rate of about 9 ml per minute and the sodium chondroitin sulfate solution was pumped to the capillary orifice at a rate of about 1 ml per minute. Spermine alginate microcapsules undergo substantial syneresis. In order to obtain microcapsules in the median size range of 5 microns, the sodium alginate solution was delivered to the capillary orifice at a nominal rate of 2 ml per minute.

Microencapsulation using decylamine-carboxymethylcellulose (CMC) was performed as follows. Sodium carboxymethylcellulose N.F., medium viscosity, (Ruger Chemical Co., Fairlawn, N.J.) and solutions of it were allowed to hydrate for at least 24 hours before use. Decylamine (Aldrich Chemical Co., Milwaukee, Wis.) was solubilized in water by titration to pH 7.0 with acetic acid (Fisher Scientific Co., Pittsburgh, Pa.). Decylamine-CMC microcapsules containing BHV-1-gD were similarly generated by thoroughly mixing graded volumes of vaccine with separate 0.75 ml volumes of 1% w/v sodium carboxymethylcellulose and enough water to make 5 ml, and acoustically pulsing the resulting mixture into 20 ml of 0.5% w/v decylamine adjusted to pH 7.0±0.1 with acetic acid.

Sodium alginate and decylamine carboxymethylcellulose microcapsule formulations were washed three times; those of spermine chondroitin sulfate once by centrifugation (20, 000 gxm), decanting, resuspending in water, and again centrifuging.

To determine capture efficiencies for BHV-1-gD, microcapsules composed of either spermine-alginate or decylamine-CMC were disrupted with 8 M sodium phosphate buffer, and those composed of spermine-chondroitin were disrupted with 1% sodium chloride. Quantities of captured antigen were compared with quantities of starting material to determine capture efficiencies.

To determine how long viral proteins were contained within microcapsules, BHV-1-gD was microencapsulated in either spermine-alginate or spermine chondroitin sulfate and stored at 4° C. for 42 days. Aliquots of microcapsules were taken at various intervals after formation, washed, and tested for the presence of captured antigen by disrupting samples as described above.

ELISA to detect BHV-1-gD:

Individual wells of flat-bottomed, 96-well plates (MAXISORPO, Nunc, Naperville, Ill.) were coated with 100 μl of rabbit anti-BHV-1-gD diluted 1:10,000 in a sodium borate solution and incubated overnight in a humidified chamber at 4° C. Wells were washed 4 times with 300 μl PBS containing 0.5% Tween 20 (Sigma, St. Louis, Mo.) (PBST). Four serial 2-fold dilutions of samples to be tested (diluted in PBST) were added in a volume of 100 μl per well and incubated for 2 hours at 37° C. Experimental samples were compared with a standard quantity of BHV-1-gD. Eight serial 2-fold dilutions from 1:1,600 to 1:204,800 of the BHV-1-gD standard were performed. Wells containing 1 pg of rotavirus (bovine strain WC3) were used as negative controls. Wells were washed 4 times with PBST, and 100 μl of mouse anti-BHV-1-gD ascitic fluid diluted 1:4,000 in PBST were added to each well and incubated for 90 min at 37° C. Wells were washed 4 times with PBST, and 100 μl of HRP-labeled sheep anti-mouse IgG (Boehringer Mannheim Biochemicals, Indianapolis, Ind.) diluted 1:2,000 in PBST plus 1% normal rabbit serum (Sigma) were added to each well and incubated for 90 min at 37° C. Wells were washed 4 times with PBST, and developed with 100 μl per well of peroxidase substrate (ABTS, Kirkegaard & Perry Laboratories, Gaithersburg, Md.). Colorimetric changes were determined at an optical density (OD) of 405 nm on a microplate ELISA reader (Dynatech MR4000, Dynatech Labs., Chantilly, VA.). The reaction was considered complete when the BHV-1-gD standard diluted 1:12,800 was 1.0 (+/−0.1) OD units.

To determine geometric mean titers and standard errors, samples with undetectable BHV-1-gD-specific antibody responses were assigned a value of 10.

Inoculation of Mice:

Groups of 5 adult, Swiss-Webster female mice (Taconic Breeding Laboratories, Germantown, N.Y.) were inoculated with various doses of either microencapsulated or unencapsulated preparations of BHV-1-gD intramuscularly (by quadriceps femoris) in a volume of 50 pi per leg. Blood was obtained by retro-orbital capillary plexus puncture using non-heparinized Natelson tubes (Monoject Corp., St. Louis, Mo.) at 1 and 2 months after inoculation, and tested for the presence of BHV-1-gD-specific antibodies by ELISA, as described below.

ELISA assay to detect BHV-1-oD-specific IgG:

Individual wells of flat-bottomed, 96-well plates (IMMULON® 2, Dynatech Labs, Chantilly, Va.) were coated with 50 pI containing 100 ng per well of BHV-1-gD diluted in PBS and stored in a humidified chamber at 4° C. overnight. Plates were washed once with dH2O, and 300 μl of 1% poly(vinyl alcohol) (PVA) (Aldrich Chemical Co., Milwaukee, Wis.) were added to each well and incubated for 2 hours at 37° C. Plates were washed 5 times with $dH_2O$, and 100 μl per well of serum samples (diluted 1:50 in 1% PVA) were added to each well and plates were incubated for 1 hour at 37° C. Serum from a mouse hyperimmunized with BHV-1-gD was diluted serially 2-fold from 1:200 to 1:204,800, and used as a positive control. Plates were washed 5 times with dH2O, and 100 μl per well of HRP-labelled goat anti-mouse IgG (Kirkegaard & Perry Laboratories, Gaithersburg, Md.) diluted 1:10,000 in 1% PVA were added and incubated for 1 hour at 37° C. Plates were washed 5 times with $dH_2O$, and developed with 100 pi per well of peroxidase substrate (ABTS, Kirkegaard & Perry Labs.). Colorimetric changes were determined at an OD of 405 nm on a microplate ELISA reader after a 15 min incubation. BHV-1-gD-specific antibody titers were calculated by comparison with a standard curve generated using hyperimmune antisera of known titer.

Results

The quantity of BHV-1-gD required to induce BHV-1-gD-specific antibody responses was reduced approximately 5,000-fold by microencapsulation in spermine-alginate and 3.3-fold by microencapsulation in decylamine-CMC (TABLE 1). BHV-1-gD-specific immune responses were not enhanced after microencapsulation in spermine-chondroitin sulfate.

Capture efficiencies were not related to enhancement of antigen-specific immune responses. Microcapsules composed of decylamine-CMC were about 20 times more efficient at capturing BHV-1-gD, but 1,500 times less capable of enhancing BHV-1-gD-specific antibody responses, as compared with spermine-alginate microcapsules containing BHV-1-gD (TABLES 1 and 2). In addition, although there were no differences in the efficiencies of capture among preparations of BHV-1-gD in spermine-alginate or spermine-chondroitin sulfate, only spermine-alginate microcapsules containing BHV-1-gD enhanced antigen-specific immune responses.

BHV-1-gD was captured and retained within both spermine-alginate and spermine-chondroitin sulfate for at least 42 days (TABLE 3). Therefore, differences in enhancement of antigen-specific immune responses could not be accounted for by rapid leakage of viral proteins from microcapsules as observed in vitro.

It has now been demonstrated that a BHV-1 subunit component, in this case BHV-1-gD, can be successfully captured within the matrix of microcapsules of the invention, and that microencapsulation of the BHV-1 subunit component greatly enhances its immunogenicity.

All patents, patent applications, and publications cited above are incorporated herein by reference in their entirety.

The present invention is not to be limited in scope by the specific embodiments described, which are intended as single illustrations of individual aspects of the invention. Functionally equivalent compositions and methods are within the scope of the invention.

TABLE 1

Humoral immune responses to encapsulated or unencapsulated preparations of BHV-1-gD in mice.

| Immunogen | Dose[a] | Micro-capsular material | GMT[b] (+/− SE) of BHV-1-gD-specific antibody post-inoculation: 1 month | 2 months |
|---|---|---|---|---|
| BHV-1-gD | 2 μg | none | 30 (+/−400) | 10[c] |
| | 400 ng | | 10 | 10 |
| | 80 ng | | 10 | 10 |
| BHV-1-gD | 10 ng | Spermine-alginate | 8,800 (+/−900) | 10,200 (+/−2600) |
| | 2 ng | | 5,800 (+/−1600) | 5,800 (+/−1600) |
| | 400 pg | | 300 (+/−500) | 200 (+/−600) |
| BHV-1-gD | 10 ng | Spermine-chondroitin sulfate | 10 | 10 |
| | 2 ng | | 10 | 10 |
| | 400 pg | | 10 | 10 |

TABLE 1-continued

Humoral immune responses to encapsulated or unencapsulated preparations of BHV-1-gD in mice.

| Immunogen | Dose[a] | Microcapsular material | GMT[b] (+/− SE) of BHV-1-gD-specific antibody post-inoculation | |
|---|---|---|---|---|
| | | | 1 month | 2 months |
| BHV-1-gD | 600 ng | Decyl- | 2,200 (+/−500) | 30 (+/−400) |
| | 60 ng | amine- | 10 | 10 |
| | 6 ng | CMC | 10 | 10 |

[a]Data collected from groups of 5 mice for each dose for each treatment.
[b]GMT = geometric mean titer
[c]To determine GMT and SE, samples with undetectable BHV-1-gD-specific antibody responses were assigned a value of 10.

TABLE 2

Relative capacities of different microcapsular materials to capture BHV-1-gD.

| Antigen | Microcapsular material | Amt. antigen available | Amt. antigen captured | Capture efficiency |
|---|---|---|---|---|
| BHV-1-gD | Spermine-alginate | 46 μg | 256 ng | 0.56% |
| | | 31.5 μg | 156 ng | 0.5% |
| | | 18 μg | 126 ng | 0.7% |
| | | 9.4 μg | 34 μg | 0.36% |

TABLE 2-continued

Relative capacities of different microcapsular materials to capture BHV-1-gD.

| Antigen | Microcapsular material | Amt. antigen available | Amt. antigen captured | Capture efficiency |
|---|---|---|---|---|
| BHV-1-gD | Spermine-chondroitin sulfate | 63 μg | 103 ng | 0.16% |
| | | 31 μg | 115 ng | 0.37% |
| | | 15 μg | 59 ng | 0.39% |
| | | 7.6 μg | 41 ng | 0.54% |
| BHV-1-gD | Decylamine-CMC | 11 μg | 1.4 μg | 12.7% |

TABLE 3

Long-term stability of BHV-1-gD in microcapsules.[a]

| Antigen | Microcapsular material | Amt. antigen remaining in microcapsules at various intervals (days) after formation | | | | | | |
|---|---|---|---|---|---|---|---|---|
| | | 0 | 1 | 3 | 7 | 14 | 28 | 42 |
| BHV-1-gD | Spermine-alginate | 12 ng | 12 ng | 12 ng | 10 ng | 8 ng | 6 ng | 4 ng |
| BHV-1-gD | Spermine-chondroitin sulfate | 38 ng | 36 ng | 38 ng | 38 ng | 36 ng | 35 ng | 34 ng |

[a]After capture in microcapsules, amount of antigen remaining at various intervals was determined by disruption of aliquots of microcapsules.

---

What is claimed is:

1. A microcapsule comprising an anisotropic Lewis salt membrane encapsulating an aqueous core and an immunogenic composition surrounded by the salt membrane, said salt membrane comprising a precipitate resulting from the interfacial reaction of spermine and alginic acid or the interfacial reaction of a water-soluble neutral salt of spermine and a water-soluble neutral salt of alginic acid, said immunogenic composition comprising a subunit component of bovine herpes virus-1 (3HV-1), which subunit component is SHV-1-gD consisting of the amino acid sequence of amino acid residues 19 to 355 of SEQ ID NO: 2.

2. The microcapsule of claim 1, wherein the water-soluble neutral salt of spermine is selected from the group consisting of halide and low molecular weight alkanoic salts, and the water-soluble neutral salt of alginic acid is selected from the group consisting of alkali metal salts, ammonium salts, and trialkanolamine salts.

3. The microcapsule of claim 2, wherein the water-soluble neutral salt of spermine is spermine hydrochloride and the water-soluble neutral salt of alginic acid is sodium alginate.

4. A method of increasing the immunogenicity of BHV-1 -gD consisting of the amino acid sequence of amino acid residues 19 to 355 of SEQ ID NO: 2, comprising encapsulating said BHV-1-gD in a microcapsule comprising an anisotropic Lewis salt membrane encapsulating an aqueous core, said salt membrane comprising a precipitate resulting from the interfacial reaction of spermine and alginic acid or the interfacial reaction of a water-soluble neutral salt of spermine and a water-soluble neutral salt of alginic acid.

5. The method of claim 4, wherein the water-soluble neutral salt of spermine is selected from the group consisting of halide and low molecular weight alkanoic salts, and the water-soluble neutral salt of alginic acid is selected from the group consisting of alkali metal salts, ammonium salts, and trialkanolamine salts.

6. The method of claim 5, wherein the water-soluble neutral salt of spermine is spermine hydrochloride and the water-soluble neutral salt of alginic acid is sodium alginate.

7. A vaccine for immunizing a member of a bovine species against BHV-1, comprising an immunogenic amount of microcapsules comprising an anisotropic Lewis salt membrane encapsulating an aqueous core and an immunogenic composition surrounded by the salt membrane, said salt membrane comprising a precipitate resulting from the interfacial reaction of spermine and alginic acid or the interfacial reaction of a water-soluble neutral salt of spermine and a water-soluble neutral salt of alginic acid, said immunogenic composition comprising BHV-1-gD consisting of the amino acid sequence of amino acid residues 19 to 355 of SEQ ID NO: 2; and a veterinarily acceptable carrier.

8. The vaccine of claim 7, wherein the water-soluble neutral salt of spermine is selected from the group consisting of halide and low molecular weight alkanoic salts, and the water-soluble neutral salt of alginic acid is selected from the group consisting of alkali metal salts, ammonium salts, and trialkanolamine salts.

9. The vaccine of claim 8, wherein the water-soluble neutral salt of spermine is spermine hydrochloride and the water-soluble neutral salt of alginic acid is sodium alginate.

10. The vaccine of claim 7, further comprising an adjuvant.

11. The vaccine of claim 10, wherein the adjuvant is selected from the group consisting of the RIBI adjuvant system, alum, aluminum hydroxide gel, an oil-in-water emulsion, a water-in-oil emulsion, Block co polymer, QS-21 saponin adjuvant, SAF-M threonyl-MDP adjuvant, AMPHIGEN® mineral oil/lecithin emulsion, Quil A saponin adjuvant, monophosphoryl lipid A, and Avridine lipid-amine adjuvant.

12. A method of vaccinating a member of a bovine species against BHV-1, comprising administering to the animal a vaccine comprising an immunogenic amount of microcapsules comprising an anisotropic Lewis salt membrane encapsulating an aqueous core and an immunogenic composition surrounded by the salt membrane, said salt membrane comprising a precipitate resulting from the interfacial reaction of spermine and alginic acid or the interfacial reaction of a water-soluble neutral salt of spermine and a water-soluble neutral salt of alginic acid, said immunogenic Composition comprising BHV-1-gD consisting of the amino acid sequence of amino acid residues 19 to 355 of SEQ ID NO: 2, and a veterinarily acceptable carrier.

13. The method of claim 12, wherein the water-soluble neutral salt of spermine is selected from the group consisting of halide and low molecular weight alkanoic salts, and the water-soluble neutral salt of alginic acid is selected from the group consisting of alkali metal salts, ammonium salts, and trialkanolamine salts.

14. The method of claim 12, wherein the water-soluble neutral salt of spermine is spermine hydrochloride and the water-soluble neutral salt of alginic acid is sodium alginate.

15. The method of claim 12, wherein the vaccine further comprises an adjuvant.

16. A kit for vaccinating a member of a bovine species against BHV-1, comprising a first container comprising an immunogenic amount of microcapsules comprising an anisotropic Lewis salt membrane encapsulating an aqueous core and an immunogenic composition surrounded by the salt membrane, said salt membrane comprising a precipitate resulting from the interfacial reaction of spermine and alginic acid or the interfacial reaction of a water-soluble neutral salt of spermine and a water-soluble neutral salt of alginic acid, said immunogenic composition comprising BHV-1-gD consisting of the amino acid sequence of amino acid residues 19 to 355 of SEQ ID NO: 2; and a second container comprising a diluent.

17. The kit of claim 16, wherein the water-soluble neutral salt of spermine is selected from the group consisting of halide and low molecular weight alkanoic salts, and the water-soluble neutral salt of alginic acid is selected from the group consisting of alkali metal salts, ammonium salts, and trialkanolamine salts.

18. The kit of claim 17, wherein the water-soluble neutral salt of spermine is spermine hydrochloride and the water-soluble neutral salt of alginic acid is sodium alginate.

19. The kit of claim 16, wherein the microcapsules are lyophilized.

* * * * *

UNITED STATES PATENT AND TRADEMARK OFFICE
CERTIFICATE OF CORRECTION

PATENT NO. : 6,270,800 B1  Page 1 of 1
DATED : August 7, 2001
INVENTOR(S) : Tully J. Speaker, H. Fred Clark, Charlotte Moser, Paul A. Offit, Manuel Campos, Patrick J. Frenchick It is certified that error appears in the above-identified patent and that said Letters Patent is hereby corrected as shown below:

Title page,
Item [73], Assignee, in addition to "Pfizer Inc.", please also add -- Temple University, Philadelphia, Pa, and The Children's Hospital of Philadelphia, Philadelphia, Pa. --.

Column 31, claim 1,
Line 44, "3HV-1" should instead read -- BHV-1 --;
Line 45, "SHV-1gD" should instead read -- BHV-1-gD --.

Signed and Sealed this

Fifth Day of March, 2002

Attest:

JAMES E. ROGAN
Attesting Officer   Director of the United States Patent and Trademark Office